United States Patent
Levy

(10) Patent No.: US 11,773,097 B2
(45) Date of Patent: *Oct. 3, 2023

(54) POLYMORPHS OF SEPIAPTERIN AND SALTS THEREOF

(71) Applicant: PTC Therapeutics MP, Inc., South Plainfield, NJ (US)

(72) Inventor: Daniel E. Levy, San Mateo, CA (US)

(73) Assignee: PTC Therapeutics MP, Inc., South Plainfield, NJ (US)

( * ) Notice: Subject to any disclaimer, the term of this patent is extended or adjusted under 35 U.S.C. 154(b) by 178 days.

This patent is subject to a terminal disclaimer.

(21) Appl. No.: 17/342,910

(22) Filed: Jun. 9, 2021

(65) Prior Publication Data

US 2021/0300930 A1  Sep. 30, 2021

Related U.S. Application Data

(63) Continuation of application No. 16/464,771, filed as application No. PCT/US2017/063517 on Nov. 28, 2017, now Pat. No. 11,072,614.

(60) Provisional application No. 62/546,390, filed on Aug. 16, 2017, provisional application No. 62/427,686, filed on Nov. 29, 2016.

(51) Int. Cl.
| | | |
|---|---|---|
| A61K 31/495 | (2006.01) | |
| A61P 3/00 | (2006.01) | |
| A61P 5/00 | (2006.01) | |
| A61P 25/00 | (2006.01) | |
| C07D 475/04 | (2006.01) | |

(52) U.S. Cl.
CPC .................. *C07D 475/04* (2013.01)

(58) Field of Classification Search
CPC . A61K 31/495; A61P 3/00; A61P 5/00; A61P 25/00; C07D 475/04
See application file for complete search history.

(56) References Cited

U.S. PATENT DOCUMENTS

| | | |
|---|---|---|
| 4,758,571 A | 7/1988 | Curtius et al. |
| 4,774,244 A | 9/1988 | Curtius et al. |
| 5,736,343 A | 4/1998 | Landry |
| 7,566,462 B2 | 7/2009 | Jungles et al. |
| 7,566,714 B2 | 7/2009 | Oppenheimer et al. |
| 7,582,799 B2 | 9/2009 | Yoshino et al. |
| 7,612,073 B2 | 11/2009 | Oppenheimer et al. |
| 7,727,987 B2 | 6/2010 | Moser et al. |
| 7,732,599 B2 | 6/2010 | Moser et al. |
| 7,947,681 B2 | 5/2011 | Oppenheimer et al. |
| 8,003,126 B2 | 8/2011 | Jungles et al. |
| 8,067,416 B2 | 11/2011 | Oppenheimer et al. |
| 8,188,043 B2 | 5/2012 | Cooke et al. |
| 8,222,422 B2 | 7/2012 | Hashimoto et al. |
| RE43,797 E | 11/2012 | Oppenheimer et al. |
| 8,318,745 B2 | 11/2012 | Moser et al. |
| 8,410,264 B2 | 4/2013 | Dai et al. |
| 9,181,254 B2 | 11/2015 | Yoshino et al. |
| 9,212,183 B2 | 12/2015 | Sieger et al. |
| 9,433,624 B2 | 9/2016 | Oppenheimer et al. |
| 9,492,451 B2 | 11/2016 | Rustomjee et al. |
| 9,993,481 B2 | 6/2018 | Oppenheimer et al. |
| 11,072,614 B2 | 7/2021 | Levy |
| 11,130,760 B2 | 9/2021 | Yoshino et al. |
| 11,173,158 B2 | 11/2021 | Hasegawa et al. |
| 2006/0040946 A1 | 2/2006 | Oppenheimer et al. |
| 2007/0270581 A1 | 11/2007 | Jungles et al. |
| 2008/0075666 A1 | 3/2008 | Dudley et al. |
| 2010/0130500 A1 | 5/2010 | Kakkis |
| 2011/0144117 A1 | 6/2011 | Widmann et al. |
| 2013/0108694 A1 | 5/2013 | Chou et al. |
| 2013/0237543 A1 | 9/2013 | Oppenheimer et al. |
| 2013/0336975 A1 | 12/2013 | Dutzar et al. |
| 2018/0078557 A1 | 3/2018 | Hasegawa et al. |
| 2020/0009145 A1 | 1/2020 | Hasegawa et al. |
| 2020/0010469 A1 | 1/2020 | Yoshino et al. |
| 2020/0061070 A1 | 2/2020 | Levy |
| 2021/0161901 A1 | 6/2021 | Smith et al. |
| 2021/0220363 A1 | 7/2021 | Smith et al. |
| 2021/0269443 A1 | 9/2021 | Levy et al. |
| 2022/0081443 A1 | 3/2022 | Yoshino et al. |

FOREIGN PATENT DOCUMENTS

| | | |
|---|---|---|
| CN | 1905863 A | 1/2007 |
| CN | 101678025 A | 3/2010 |
| CN | 104736539 A | 6/2015 |
| JP | S59-25323 A | 2/1984 |
| JP | 2007-511536 A | 5/2007 |
| JP | 2008-520574 A | 6/2008 |
| JP | 2010-523708 A | 7/2010 |

(Continued)

OTHER PUBLICATIONS

Opladen et al., "Consensus guideline for the diagnosis and treatment of tetrahydrobiopterin ($BH_4$) deficiencies." Orphanet J Rare Dis. 15(1):126 (2020) (30 pages).
English Translation of Office Action for Japanese Patent Application No. 2019-548533, dated Oct. 20, 2021 (10 pages).
Office Action for Japanese Patent Application No. 2019-548534, dated Oct. 26, 2021 (10 pages).
Makoto, "Analysis of salt selection of current active pharmaceutical ingredients," Yakuzaigaku. 73(3): 176 (2013).
Shircks Laboratories, "Data Sheet: Tetrahydrobioterin Tablets," published Jul. 1, 2009 (1 page).

(Continued)

*Primary Examiner* — Bruck Kifle
(74) *Attorney, Agent, or Firm* — Clark & Elbing LLP

(57) ABSTRACT

Disclosed are crystalline forms of sepiapterin free base selected from polymorphs A, B, C, D, E, F, and G, and combinations thereof, as well as crystalline polymorphs of salts of sepiapterin. Also disclosed are pharmaceutical compositions containing one or more such polymorphs and methods for preparing such polymorphs. Sepiapterin is useful in the treatment of a number diseases associated with low cellular levels of BH4, for example, phenylketonuria.

17 Claims, 11 Drawing Sheets

(56) References Cited

FOREIGN PATENT DOCUMENTS

| JP | 2012-207029 A | 10/2012 |
|---|---|---|
| JP | 2013-502396 A | 1/2013 |
| JP | 2014-015477 A | 1/2014 |
| WO | WO-2005/028462 A1 | 3/2005 |
| WO | WO-2005/049000 A2 | 6/2005 |
| WO | WO-2008/128049 A2 | 10/2008 |
| WO | WO-2010/072776 A1 | 7/2010 |
| WO | WO-2011/132435 A1 | 10/2011 |
| WO | WO-2013/168693 A1 | 11/2013 |
| WO | WO-2018/019931 A1 | 2/2018 |
| WO | WO-2018/102314 A1 | 6/2018 |
| WO | WO-2018/102315 A1 | 6/2018 |
| WO | WO-2018/195321 A1 | 10/2018 |
| WO | WO-2019/046849 A1 | 3/2019 |
| WO | WO-2021/026247 A1 | 2/2021 |
| WO | WO-2021/062264 A1 | 4/2021 |

OTHER PUBLICATIONS

Takada, "API form screening and selection in drug discovery stage," Pharm Stage. 6(10):20-25 (2007) (9 pages).
Yoshinaki, "Organic compound crystal production handbook," 10-11,57, 72-78, 81 (2008).
Abell et al., "Effect of oral CNSA-001 (sepiapterin, PTC923) on gastric accommodation in women with diabetic gastroparesis: a randomized, placebo-controlled, phase 2 trial," J Diabetes Complications. 35(9):107961 (2021) (7 pages).
Bratkovic et al., "PTC923 (sepiapterin) lowers elevated blood phenylalanine in subjects with phenylketonuria: a phase 2 randomized, multi-center, three-period crossover, open-label, active controlled, all-comers study," Metabolism. 128:155116 (2021) (8 pages).
Smith et al., "Exploratory study of the effect of one week of orally administered CNSA-001 (sepiapterin) on CNS levels of tetrahydrobiopterin, dihydrobiopterin and monoamine neurotransmitter metabolites in healthy volunteers," Mol Genet Metab Rep. 21:100500 (2019) (3 pages).
U.S. Appl. No. 17/059,632, PTC Therapeutics MP, Inc.
U.S. Appl. No. 17/059,719, PTC Therapeutics MP, Inc.
U.S. Appl. No. 17/059,887, PTC Therapeutics MP, Inc.
Balbach et al., "Pharmaceutical evaluation of early development candidates 'the 100 mg-approach'," Int J Pharm. 275(1-2):1-12 (2004).
Bernegger et al., "High frequency of tetrahydrobiopterin-responsiveness among hyperphenylalaninemias: a study of 1,919 patients observed from 1988 to 2002," Mol Genet Metab. 77(4):304-13 (2002).
Blau et al., "Tetrahydrobiopterin deficiencies without hyperphenylalaninemia: diagnosis and genetics of DOPA-responsive dystonia and sepiapterin reductase deficiency," Mol Genet Metab. 74(1-2):172-85 (2001).
Brittain et al., "Polymorphism in Pharmaceutical Solids," CRC Press. 192:3-480 (2016).
Caira, "Crystalline polymorphism of organic compounds," Topics in Current Chemistry. 198:163-208 (1998).
Clinical Trials "A Study of CNSA-001 in Primary Tetrahydrobiopterin (BH4) Deficient Participants with Hyperphenylalaninemia," (printed on Feb. 11, 2021).
Curtius et al., "Atypical phenylketonuria due to tetrahydrobiopterin deficiency. Diagnosis and treatment with tetrahydrobiopterin, dihydrobiopterin and sepiapterin." Clin Chim Acta. 93(2):251-62 (1979).
Examination Report No. 1 issued for Australian Patent Application No. 2017366879, dated Feb. 25, 2021 (6 pages).
Extended European Search Report issued in European Application No. 17876202.7, dated Aug. 5, 2020 (11 pages).
Grant et al., "Relationships among rat ultrasonic vocalizations, behavioral measures of striatal dopamine loss, and striatal tyrosine hydroxylase immunoreactivity at acute and chronic time points following unilateral 6-hydroxydopamine-induced dopamine depletion," available in PMC Sep. 15, 2016, published in final edited form as: Behav Brain Res. 291:361-71 (2015) (24 pages).
Hennermann et al., "Partial and total tetrahydrobiopterin-responsiveness in classical and mild phenylketonuria (PKU)," J Inherit Metab Dis. 25(Suppl 1):21:041-P (2002) (Abstract only).
Ichiyama et al., "Enzymic studies on the biosynthesis of serotonin in mammalian brain," J Biol Chem. 245(7):1699-709 (1970).
International Search Report and Written Opinion for International Application No. PCT/US17/63517, dated Feb. 15, 2018 (18 pages).
Kaufman, "Phenylalanine hydroxylation cofactor in phenylketonuria," Science. 128(3337):1506-8 (1958).
Klaiman et al., "Tetrahydrobiopterin as a treatment for autism spectrum disorders: a double-blind, placebo-controlled trial," J Child Adolesc Psychopharmacol. 23(5):320-8 (2013) (11 pages).
Kuplennik et al., "Enhanced nanoencapsulation of sepiapterin within PEG-PCL nanoparticles by complexation with triacetyl-beta cyclodextrin," Molecules. 24(15):2715 (2019).
Kure et al., "Tetrahydrobiopterin-responsive phenylalanine hydroxylase deficiency," J Pediatr. 135(3):375-8(1999).
Kwon et al., "Reduced biopterin as a cofactor in the generation of nitrogen oxides by murine macrophages," J Biol Chem. 264(34):20496-501 (1989).
Matalon et al., "Tetrahydrobiopterin (BH$_4$) responsive phenylalanine hydroxylase (PAH) mutations," J Inherit Metab Dis. 25(Suppl 1):23:045-P (2002) (Abstract only).
Mayer et al., "Brain nitric oxide snythase is a biopterin- and flavin-containing multi-functional oxido-reductase," FEBS Lett. 288(1-2):187-91 (1991).
Muntau et al., "Tetrahydrobiopterin as an alternative treatment for mild phenylketonuria," N Engl J Med. 347(26):2122-32 (2002).
Nagatsu et al., "Tyrosine hydroxylase. The initial step in norepinephrine biosynthesis," J Biol Chem. 239(9):2910-7 (1964).
Niederwieser et al., "Atypical phenylketonuria with defective biopterin metabolism. Monotherapy with tetrahydrobiopterin or sepiapterin, screening and study of biosynthesis in man," Eur J Pediatr. 138(2):110-2 (1982).
Nord "Tetrahydrobiopterin Deficiency," (online PD Sep. 2016).
Park et al., "Optimization of expression conditions enhances production of sepiapterin, a precursor for tetrahydrobiopterin biosynthesis, in recombinant *Escherichia coli*," J Microbiol Biotechnol. 25(10):1709-13 (2015).
Partial Suppelmentary European Search Report issued in European Patent Application No. 17876202.7, dated May 4, 2020 (15 pages).
Pfleiderer et al., "Pteridine, LXVIII. Überführung von biopterin in sepiapterin und absolute konfiguration des sepiapterins," Chem Ber. 112:2750-2755 (1979).
Ponzone et al., "Hyperphenylalaninemia and pterin metabolism in serum and erythrocytes," Clin Chim Acta. 216(1-2):63-71 (1993).
Saeed et al., "Uncertainty of thermal characterization of phase change material by differential scanning calorimetry analysis," Int J Eng Res Technol. 5(1):405-12 (2016).
Sawabe et al., "Cellular uptake of sepiapterin and push-pull accumulation of tetrahydrobiopterin," Mol Genet Metab. 94(4):410-6 (2008).
Sawabe et al., Sepiapterin administration raises tissue BH4 levels more efficiently than BH$_4$ supplement in normal mice, *Chemistry and Biology of Pteridines and Folates*. Ed. Milstien et al., pp. 199-204 (2001).
Schircks et al., "Über Pterinchemie. 65 Mitteilung [1]. Herstellung von (6 R,S)-5,6,7,8-Tetrahydro-L-biopterin, 7,8-Dihydro-L-biopterin, L-Sepiapterin, Deoxysepiapterin, (6 R,S)-5,6-Dihydrodeoxysepiapterin and 2'-Deoxybiopterin," Helv Chim Acta. 61(7): 2731-8 (1978).
Shircks Laboratories, "Data Sheet: L-Sepiapterin. Product No. 11.225," published Jan. 26, 2016 (1 page).
Singhal et al., "Drug polymorphism and dosage form design: a practical perspective," Adv Drug Deliv Rev. 56(3):335-47 (2004).
Smith et al., "Phase I clinical evaluation of CNSA-001 (sepiapterin), a novel pharmacological treatment for phenylketonuria and tetrahydrobiopterin deficiencies, in healthy volunteers," Mol Genet Metab.126(4):406-12 (2019).

(56) References Cited

OTHER PUBLICATIONS

Spaapen et al., "Tetrahydrobiopterin-responsive phenylalanine hydroxylase deficiency, state of the art," Mol Genet Metab. 78(2):93-9 (2003).
Sugiura et al., "The structures of the reoxidation products of 7,8-dihydroneopterin," Bull Chem Soc Jpn. 46(3):939-42(1973).
Tietz et al., "A new pteridine-requiring enzyme system for the oxidiation of glyceryl ethers," J Biol Chem. 239(12):4081-90 (1964).
Viscontini et al., "Fluorescent substances from *Drosophilia melanogaster*. XII. The yellow fluorescent pterine: sepiapterin and isosepiapterin," Helvetica Chimica Acta. 42:836-41 (1959).
Woo et al., "Production of sepiapterin in *Escherichia coli* by coexpression of cyanobacterial GTP cyclohydrolase I and human 6-pyruvoyltetrahydropterin synthase," Appl Environ Microbiol. 68(6):3138-3140 (2002).

POLYMORPHS OF SEPIAPTERIN AND SALTS THEREOF

BACKGROUND OF THE INVENTION

Sepiapterin is a naturally occurring precursor of tetrahydrobiopterin (BH4), a naturally occurring essential cofactor of critical intracellular enzymes to include but not limited to phenylalanine hydroxylase (PAH) (Kaufman, 1958), tyrosine hydroxylase (TH) (Nagatsu et al, 1964), tryptophan hydroxylase (TPH) (Ichiyama et al, 1970), nitric oxide synthases (NOS) (Kwon et al, 1989), (Mayer et al, 1991) and alkylglycerol monooxygenase (AGMO) (Tietz et al, 1964). Rapid conversion of sepiapterin to BH4 favoring accumulation of BH4 occurs via a two-step reduction in the salvage pathway for BH4 synthesis (Sawabe, 2008). A synthetic form of BH4 (e.g., sapropterin dihydrochloride) is used as a therapy for diseases associated with high plasma phenylalanine, such as phenylketonuria (PKU). PKU is an inborn error of metabolism caused predominantly by mutations in the PAH gene. BH4 was also tested as a therapy for various central nervous symptoms associated with PKU and other diseases, but demonstrated limited effect, presumably due to the inability of BH4 to effectively cross the blood brain barrier (Klaiman et al, 2013; Grant et al, 2015).

Recent work has suggested that, compared with BH4, peripherally administered sepiapterin possesses greater permeability through membranes and as a result, can more readily access liver, kidney, and brain cells. It is reported that sepiapterin is rapidly converted into BH4 intracellularly via the tetrahydrobiopterin-salvage pathway, thereby elevating liver, kidney, and brain BH4 levels (Sawabe, 2008). As a result, sepiapterin may serve as a useful therapeutic for diseases associated with low intracellular BH4 levels or with dysfunction of various BH4 dependent metabolic pathways.

Sepiapterin herein is the S-enantiomer and has the formula (IA) and formula (IB)

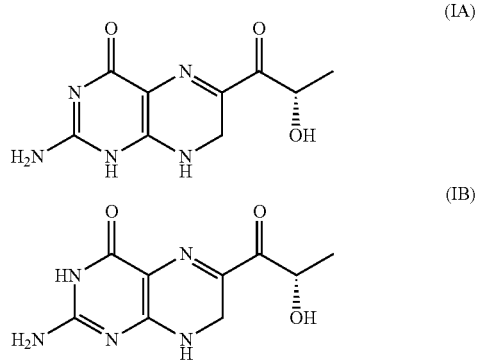

It is known that sepiapterin has limited stability in solutions. Furthermore, certain forms of solid sepiapterin degrade under oxidative conditions even at room temperature and in the presence of light.

Accordingly, there exists an unmet need for stable solid-state forms of sepiapterin.

BRIEF SUMMARY OF THE INVENTION

The invention provides a solid form of sepiapterin free base, wherein the solid form comprises an amorphous form of sepiapterin free base, a single polymorph form of sepiapterin free base, a mixture of polymorph forms of sepiapterin free base, a salt of sepiapterin or a mixture of salts of sepiapterin, or a combination thereof, with the proviso that the solid form is not a pure polymorph of Form A or Form E sepiapterin free base.

The invention also provides crystalline polymorph forms of salts of sepiapterin, or a mixture thereof. As an example, the invention provides a crystalline polymorph form of sepiapterin hydrochloride salt.

It has now been surprisingly found that under certain conditions, new crystalline forms of sepiapterin free base and acid salts are formed, which have advantageous utilities and properties. The invention thus provides methods for preparing the various polymorphic forms.

The invention further provides pharmaceutical compositions comprising one or more of these polymorphic forms.

In an aspect, the invention features a crystalline form sepiapterin having at least one peak at diffraction angle 2θ (°) of 8.4°±0.5, 16.9°±0.5, or 25.4°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 8.4°±0.5, 16.9°±0.5, and 25.4°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 14.9°±0.5, or 34.1°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 8.4°±0.5, 14.9°±0.5, 16.9°±0.5, 25.4°±0.5, and 34.1°±0.5 as measured by X-ray diffractometry by irradiation with Cu Kα X-rays or calculated from X-ray diffractometry.

In some embodiments, the crystalline form of sepiapterin has the X-ray powder diffraction spectrum as shown in FIG. 1. In some embodiments, the crystalline form of sepiapterin has an endothermic onset at about 195° C. in differential scanning calorimetry (DSC) profile.

In an aspect, the invention features crystalline form sepiapterin having at least one peak at diffraction angle 2θ (°) of 5.7°±0.5, 7.8°±0.5, or 25.4°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 5.7°±0.5, 7.8°±0.5, and 25.4°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 9.1°±0.5, 11.5°±0.5, 15.3°±0.5, 16.0°±0.5, 20.1°±0.5, or 26.6°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 5.7°±0.5, 7.8°±0.5, 9.1°±0.5, 11.5°±0.5, 15.3°±0.5, 16.0°±0.5, 20.1°±0.5, 25.4°±0.5, and 26.6°±0.5 as measured by X-ray diffractometry by irradiation with Cu Kα X-rays or calculated from X-ray diffractometry.

In some embodiments, the crystalline form of sepiapterin has the X-ray powder diffraction spectrum as shown in FIG. 2. In some embodiments, the crystalline form of sepiapterin has an endothermic onset at about 58° C., 102° C., 130° C., 156.5° C., or 168° C. in differential scanning calorimetry (DSC) profile. In some embodiments, the crystalline form of sepiapterin has an endothermic onset at about 58° C., 102° C., 130° C., 156.5° C., and 168° C. in differential scanning calorimetry (DSC) profile.

In an aspect, the invention features a crystalline form sepiapterin having at least one peak at diffraction angle 2θ (°) of 8.9°±0.5, 10.3°±0.5, or 26.0°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 8.9°±0.5, 10.3°±0.5, and 26.0°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 10.9°±0.5, 17.8°±0.5, 24.9°±0.5, 26.7°±0.5, 26.8°±0.5, or 28.3°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 8.9°±0.5, 10.3°±0.5, 10.9°±0.5, 17.8°±0.5, 24.9°±0.5, 26.0°±0.5, 26.7°±0.5, 26.8°±0.5, and 28.3°±0.5 as measured by X-ray diffractometry by irradiation with Cu Kα X-rays or calculated from X-ray diffractometry.

In some embodiments, the crystalline form of sepiapterin has the X-ray powder diffraction spectrum as shown in FIG. 3. In some embodiments, the crystalline form of sepiapterin has an endothermic onset at about 43° C., 66° C., or 233° C. in differential scanning calorimetry (DSC) profile. In some embodiments, the crystalline form of sepiapterin has an endothermic onset at about 43° C., 66° C., and 233° C. in differential scanning calorimetry (DSC) profile.

In an aspect, the invention features a crystalline form sepiapterin having at least one peak at diffraction angle 2θ (°) of 9.7°±0.5, 10.2°±0.5, or 11.3°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 9.7°±0.5, 10.2°±0.5, and 11.3°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 14.0°±0.5, 14.6°±0.5, 19.9°±0.5, 22.2°±0.5, 25.3°±0.5, or 32.4°±0.5 as measured by X-ray diffractometry by irradiation with Cu Kα X-rays or calculated from X-ray diffractometry. In some embodiments, the crystalline form of sepiapterin has at least one peak at diffraction angle 2θ (°) of 9.7°±0.5, 10.2°±0.5, 11.3°±0.5, 14.0°±0.5, 14.6°±0.5, 19.9°±0.5, 22.2°±0.5, 25.3°±0.5, and 32.4°±0.5 as measured by X-ray diffractometry by irradiation with Cu Kα X-rays or calculated from X-ray diffractometry.

In some embodiments, the crystalline form of sepiapterin has the X-ray powder diffraction spectrum as shown in FIG. 4. In some embodiments, the crystalline form of sepiapterin has an endothermic onset at about 113° C. or 196° C. in differential scanning calorimetry (DSC) profile. In some embodiments, the crystalline form of sepiapterin has an endothermic onset at about 113° C. and 196° C. in differential scanning calorimetry (DSC) profile.

In an aspect, the invention features a composition including any of the foregoing crystalline forms of sepiapterin, or combinations thereof. In some embodiments of the composition, the crystalline form of sepiapterin of any one of claims 1 to 27, is present in an amount of at least 90 percent by weight of the composition.

In an aspect, the invention features a pharmaceutical composition including any of the foregoing crystalline forms of sepiapterin. In some embodiments, the crystalline form of sepiapterin is formulated as particles between 50 µm and 250 µm in size (e.g., less than 100 µm in size).

In an aspect, the invention features a method for preparing a crystalline form of sepiapterin including preparing a slurry of a first crystalline form of sepiapterin in water, acetone/water, isopropanol/isopropyl acetate, or tetrahydrofuran/n-hexane, isolating the solids from the slurry, and drying the solids. In some embodiments, the slurry of the first crystalline form of sepiapterin is stirred at 25-75° C. for 6-72 hours. In some embodiments, the solids are dried at 20-30° C. for 6-24 hours. In some embodiments, the solids are dried at 40-60° C. for 5-10 hours. In some embodiments, the solids are dried at atmospheric pressure. In some embodiments, the solids are dried under vacuum.

In an aspect, the invention features a salt of sepiapterin. In some embodiments, the salt of sepiapterin is the methanesulfonate salt, the nicotinate salt, the p-toluenesulfonate salt, the benzenesulfonate, the phosphate salt, the malonate salt, the tartrate salt, the gentisate salt, the fumarate salt, the glycolate salt, the acetate salt, the sulfate salt, or the hydrochloride salt.

In an aspect, the invention features a crystalline form of a salt of sepiapterin, wherein the crystalline form of a salt of sepiapterin is:

(a) a crystalline form of the methanesulfonate salt of sepiapterin having at least one peak at diffraction angle 2θ (°) of 7.8°±0.5, 23.5°±0.5, and/or 29.0°±0.5 as measured by X-ray diffractometry by irradiation with Cu Kα X-rays or calculated from X-ray diffractometry;

(b) a crystalline form of the methanesulfonate salt of sepiapterin having at least one peak at diffraction angle 2θ (°) of 21.7°±0.5, 26.0°±0.5, and/or 28.9°±0.5 as measured by X-ray diffractometry by irradiation with Cu Kα X-rays or calculated from X-ray diffractometry (c) a crystalline form of the nicotinate salt of sepiapterin having at least one peak at diffraction angle 2θ (°) of 9.5°±0.5, 9.9°±0.5, and/or 24.5°±0.5 as measured by X-ray diffractometry by irradiation with Cu Kα X-rays or calculated from X-ray diffractometry;

(d) a crystalline form of the p-toluenesulfonate salt of sepiapterin having at least one peak at diffraction angle 2θ (°) of 6.5°±0.5, 15.1°±0.5, and/or 23.4°±0.5 as measured by X-ray diffractometry by irradiation with Cu Kα X-rays or calculated from X-ray diffractometry;

(e) a crystalline form of the benzenesulfonate salt of sepiapterin having at least one peak at diffraction angle 2θ (°) of 6.5°±0.5, 14.8°±0.5, and/or 19.6°±0.5 as measured by X-ray diffractometry by irradiation with Cu Kα X-rays or calculated from X-ray diffractometry;

(f) a crystalline form of the phosphate salt of sepiapterin having at least one peak at diffraction angle 2θ (°) of 16.6°±0.5, 22.2°±0.5, and/or 25.6°±0.5 as measured by X-ray diffractometry by irradiation with Cu Kα X-rays or calculated from X-ray diffractometry;

(g) a crystalline form of the malonate salt of sepiapterin having at least one peak at diffraction angle 2θ (°) of 6.9°±0.5, 22.7°±0.5, and/or 23.8°±0.5 as measured by X-ray diffractometry by irradiation with Cu Kα X-rays or calculated from X-ray diffractometry;

(h) a crystalline form of the tartrate salt of sepiapterin having at least one peak at diffraction angle 2θ (°) of 7.3°±0.5, 14.2°±0.5, and/or 21.8°±0.5 as measured by X-ray diffractometry by irradiation with Cu Kα X-rays or calculated from X-ray diffractometry;

(i) a crystalline form of the gentisate salt of sepiapterin having at least one peak at diffraction angle 2θ (°) of 7.1°±0.5, 8.7°±0.5, and/or 26.7°±0.5 as measured by X-ray diffractometry by irradiation with Cu Kα X-rays or calculated from X-ray diffractometry;

(j) a crystalline form of the fumarate salt of sepiapterin having at least one peak at diffraction angle 2θ (°) of 11.3°±0.5, 24.0°±0.5, and/or 28.2°±0.5 as measured by X-ray diffractometry by irradiation with Cu Kα X-rays or calculated from X-ray diffractometry;

(k) a crystalline form of the glycolate salt of sepiapterin having at least one peak at diffraction angle 2θ (°) of 7.6°±0.5, 10.7°±0.5, and/or 24.0°±0.5 as measured by X-ray diffractometry by irradiation with Cu Kα X-rays or calculated from X-ray diffractometry;

(l) a crystalline form of the acetate salt of sepiapterin having at least one peak at diffraction angle 2θ (°) of 6.2°±0.5, 12.0°±0.5, and/or 18.1°±0.5 as measured by X-ray diffractometry by irradiation with Cu Kα X-rays or calculated from X-ray diffractometry;

(m) a crystalline form of the sulfate salt of sepiapterin having at least one peak at diffraction angle 2θ (°) of 5.1°±0.5, 7.8°±0.5, and/or 23.0°±0.5 as measured by X-ray diffractometry by irradiation with Cu Kα X-rays or calculated from X-ray diffractometry; or (n) a crystalline form of the sulfate salt of sepiapterin having at least one peak at diffraction angle 2θ (°) of 7.8°±0.5, 8.8°±0.5, and/or 24.1°±0.5 as measured by X-ray diffractometry by irradiation with Cu Kα X-rays or calculated from X-ray diffractometry.

In an aspect, the invention features a crystalline form of the hydrochloride salt of sepiapterin having at least one peak at diffraction angle 2θ (°) of 7.8°±0.5, 12.9°±0.5, and/or 26.2°±0.5 as measured by X-ray diffractometry by irradiation with Cu Kα X-rays or calculated from X-ray diffractometry In an aspect, the invention features a composition including any of the foregoing crystalline forms of a salt of sepiapterin. In some embodiments, the crystalline form of the salt of sepiapterin is present in at least 90 percent by weight.

In an aspect, the invention features a pharmaceutical composition including any of the foregoing crystalline forms of a salt of sepiapterin and a pharmaceutically acceptable carrier. In some embodiments, the crystalline form of sepiapterin is formulated as particles less than 100 μm in size.

In another aspect, the invention features a method for treating a BH4 related disorder in a patient in need thereof, the method comprising administering to the patient an effective amount of any of the foregoing crystalline forms of sepiapterin or pharmaceutical compositions. In some embodiments, the BH4-related disorder is a disease associated with low intracellular BH4 levels or with dysfunction of various BH4 dependent metabolic pathways including, but not limited to, primary tetrahydrobiopterin deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, gastroparesis, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, and hypoglycemia. Thus, the various forms of sepiapterin in accordance with the present invention can be administered to a patient in an effective amount to obtain a treatment or amelioration of the disease or dysfunction.

In another aspect, the invention features a method of increasing BH4, serotonin, and/or dopamine levels (e.g., at least 5%, 10%, 20%, 30%, 40%, 50%, 60%, 70%, 80%, 90%, 100%, 200%, 300%, 400%, 500%, 1000% or more) in a subject in need thereof, the method comprising administering to the patient an effective amount of any of the foregoing crystalline forms of sepiapterin or pharmaceutical compositions.

In another aspect, the invention features a method of decreasing phenylalanine levels (e.g., at least 5%, 10%, 20%, 30%, 40%, 50%, 60%, 70%, 80%, 90%, 100%, 200%, 300%, 400%, 500%, 1000% or more) in a subject in need thereof, the method comprising administering to the patient an effective amount of any of the foregoing crystalline forms of sepiapterin or a pharmaceutical compositions.

In another aspect, the invention features a method of increasing the activity (e.g., at least 55%, 10%, 20%, 30%, 40%, 50%, 60%, 70%, 80%, 90%, 100%, 200%, 300%, 400%, 500%, 1000% or more) of phenylalanine hydroxylase, tyrosine hydroxylase, tryptophan hydroxylase, nitric oxide synthase, and/or alkylglycerol monooxygenase in a subject, the method comprising administering to the patient an effective amount of any of the foregoing crystalline forms of sepiapterin or a pharmaceutical compositions.

In another aspect, the invention features a method of treating phenylketonuria in a subject in need thereof, the method comprising administering to the patient an effective amount of any of the foregoing crystalline forms of sepiapterin or pharmaceutical compositions.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition (e.g., a compound or a preparation that includes a compound as described herein) to a subject or system.

Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

As used herein, the term "BH4 related disorder," refers to any disease or disorder that may derive a therapeutic benefit from modulation (e.g., inhibition) of the level of BH4, e.g., phenylketonuria.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. A therapeutically effective amount also encompasses an amount sufficient to confer benefit, e.g., clinical benefit.

By "increasing the activity of phenylalanine hydroxylase," is meant increasing the level of an activity related to phenylalanine hydroxylase, or a related downstream effect. A non-limiting example of increasing an activity of phenylalanine hydroxylase is decreasing the level of phenylalanine. The activity level of phenylalanine hydroxylase may be measured using any method known in the art.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein or mRNA in a sample.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: ascorbic acid, butylated hydroxytoluene (BHT), calcium carbonate, calcium phosphate (dibasic), calcium stearate, colloidal silicon dioxide, croscarmellose, croscarmellose sodium, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" or "patient" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

BRIEF DESCRIPTION OF THE SEVERAL VIEWS OF THE DRAWING(S)

DETAILED DESCRIPTION OF THE INVENTION

Figure 1:
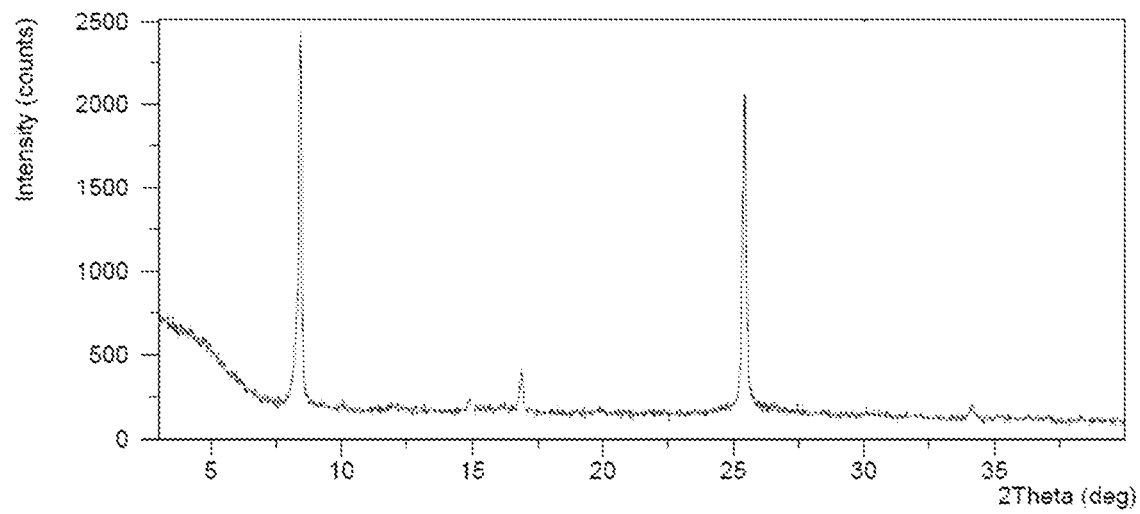
FIG. 1 shows the X-ray diffraction diagram of the crystalline Form B of sepiapterin free base.

The present invention provides a solid form of sepiapterin, wherein the solid form comprises an amorphous form, a crystalline polymorph form, a mixture of amorphous and/or crystalline polymorph forms, a salt of sepiapterin, or a combination thereof, with the proviso that the solid form of sepiapterin is not a pure polymorph Form A and/or pure polymorph Form E.

In an embodiment, in the solid form of sepiapterin the mixture comprises at least one of crystalline polymorph Form B, C, D, F, and G of sepiapterin.

In an embodiment, the solid form comprises at least one crystalline sepiapterin free base selected from polymorph Forms B, C, D, F, and G and crystalline polymorph A or E or both crystalline polymorphs A and E.

The polymorphic forms of sepiapterin free base as well as the polymorphic forms of the salts of sepiapterin may be characterized by any suitable method for studying solid state materials. In an embodiment, the polymorphic forms are characterized by X-ray powder Diffractometry (XRD). The XRD peak positions are expressed as the 2θ°. In the X-ray diagram, the angle of refraction 2θ is plotted on the horizontal axis (x-axis) and the relative peak intensity (background-corrected peak intensity) on the vertical (y-axis). X-ray powder diffraction patterns are measured on, or using instruments comparable to, a PANalytical Empyrean X-ray powder diffractometer with Cu Kα radiation source (Kα1 radiation, wavelength λ=1.54060 Angstrom, Kα2 radiation, wavelength 1.544426 Angstrom; Kα2/Kα1 intensity ratio: 0.50). The optical density of the peaks on the film is proportional to the light intensity. The film is scanned using a peak scanner.

As it relates to any of the peaks of X-ray powder diffraction set forth throughout this application, "about" refers to ±0.1, particularly ±0.05, and more particularly ±0.02 of the 2θ values in degrees.

In an embodiment, the crystalline polymorph Form B of sepiapterin is characterized by an X-ray powder diffraction pattern obtained by irradiation with Cu Kα X-rays having peaks expressed as 2θ at least at about 8.4, about 16.9, and about 25.4°.

In a particular embodiment, the crystalline polymorph Form B of sepiapterin is characterized by an X-ray powder diffraction pattern obtained by irradiation with Cu Kα X-rays having peaks expressed as 2θ at least at about 8.4, about 14.9, about 16.9, about 25.4, and about 34.1°.

In an embodiment, the crystalline polymorph Form C of sepiapterin is characterized by an X-ray powder diffraction pattern obtained by irradiation with Cu Kα X-rays having peaks expressed as 2θ at least at about 5.7, about 7.8, and about 25.4°.

In a particular embodiment, the crystalline sepiapterin polymorph Form C is characterized by an X-ray powder diffraction pattern obtained by irradiation with Cu Kα X-rays having peaks expressed as 2θ at least at about 5.7, about 7.8, about 9.1, about 11.5, about 15.3, about 16.0, about 20.1, about 25.4, and about 26.6°.

In an embodiment, the crystalline sepiapterin polymorph Form D is characterized by an X-ray powder diffraction pattern obtained by irradiation with Cu Kα X-rays having peaks expressed as 2θ at least at about 8.9, about 10.3, and about 26.0°.

In a particular embodiment, the crystalline sepiapterin polymorph Form D is characterized by an X-ray powder diffraction pattern obtained by irradiation with Cu Kα X-rays having peaks expressed as 2θ at least at about 8.9, about 10.3, about 10.9, about 17.8, about 24.9, about 26.0, about 26.7, about 26.8, and about 28.3°.

In an embodiment, the crystalline sepiapterin polymorph Form F is characterized by an X-ray powder diffraction pattern obtained by irradiation with Cu Kα X-rays having peaks expressed as 2θ at least at about 9.7, about 10.2, and about 11.3°.

In a particular embodiment, the crystalline sepiapterin polymorph Form F is characterized by an X-ray powder diffraction pattern obtained by irradiation with Cu Kα X-rays having peaks expressed as 2θ at least at about 9.7, about 10.2, about 11.3, about 14.0, about 14.6, about 19.9, about 22.2, about 25.3, and about 32.4°.

In an embodiment, the crystalline sepiapterin polymorph Form G is characterized by an X-ray powder diffraction pattern obtained by irradiation with Cu Kα X-rays having peaks expressed as 2θ at least at about 10.0, about 10.6, and about 25.7°.

In a particular embodiment, the crystalline sepiapterin polymorph Form G is characterized by an X-ray powder diffraction pattern obtained by irradiation with Cu Kα X-rays having peaks expressed as 2θ at least at about 10.0, about 10.6, about 11.2, about 15.3, about 15.9, about 22.8, about 24.4, about 25.0, about 25.7, and about 26.6°.

In an embodiment, the solid form comprises at least one crystal sepiapterin free base selected from polymorph forms B, C, D, F, and G; selected from polymorph forms B, C, and D; selected from polymorph forms B, C, and F; selected from polymorph forms D, F, and G; as well as any binary, ternary, or quaternary combinations of the polymorph forms. The solid forms indicated above could further include polymorph A and/or E.

In an embodiment, polymorph Form B, C, D, or G, or a combination thereof, is present in the solid form in an amount of at least 90 percent by weight of the solid form.

In certain embodiments, the crystalline sepiapterin free base is present in at least 70 percent or more by weight, at least 80 percent or more by weight, and preferably at least 90 percent or more by weight, based on the weight of the sepiapterin free base.

The crystalline Form A of sepiapterin free base is characterized by an X-ray powder diffraction pattern obtained by irradiation with Cu Kα X-rays having peaks expressed as 2θ at least at about 4.7°, about 7.4°, about 9.5°, about 11.3°, about 15.6°, about 26.2°, and about 27.2°.

Figure 19:
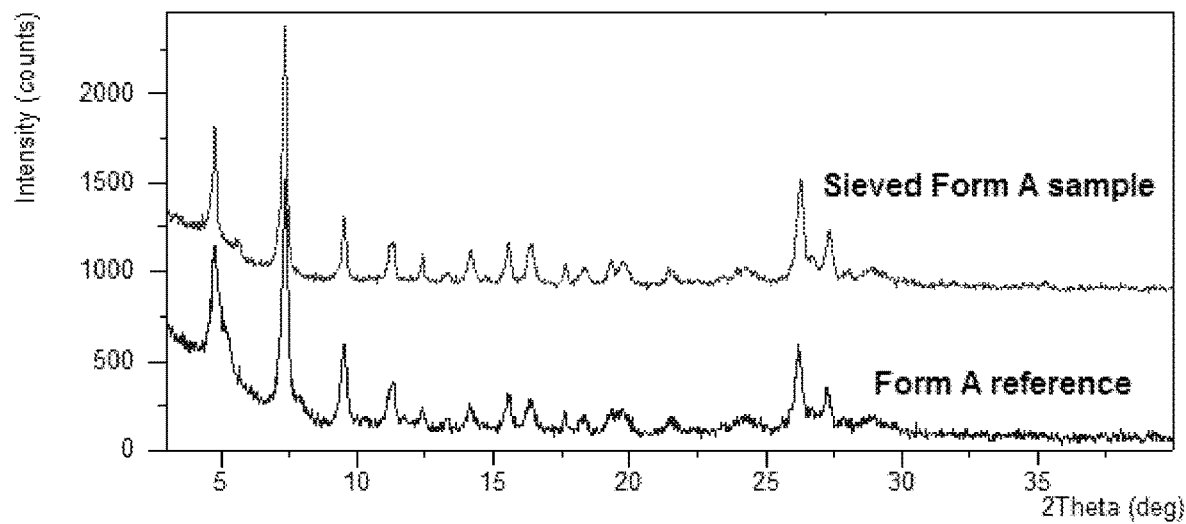
FIG. 19 shows an overlay of the X-ray diffraction diagrams of the crystalline forms of sepiapterin Form A before and after a grinding and sieving process and confirms the physical form stability thereof to grinding and sieving.
Figure 20:
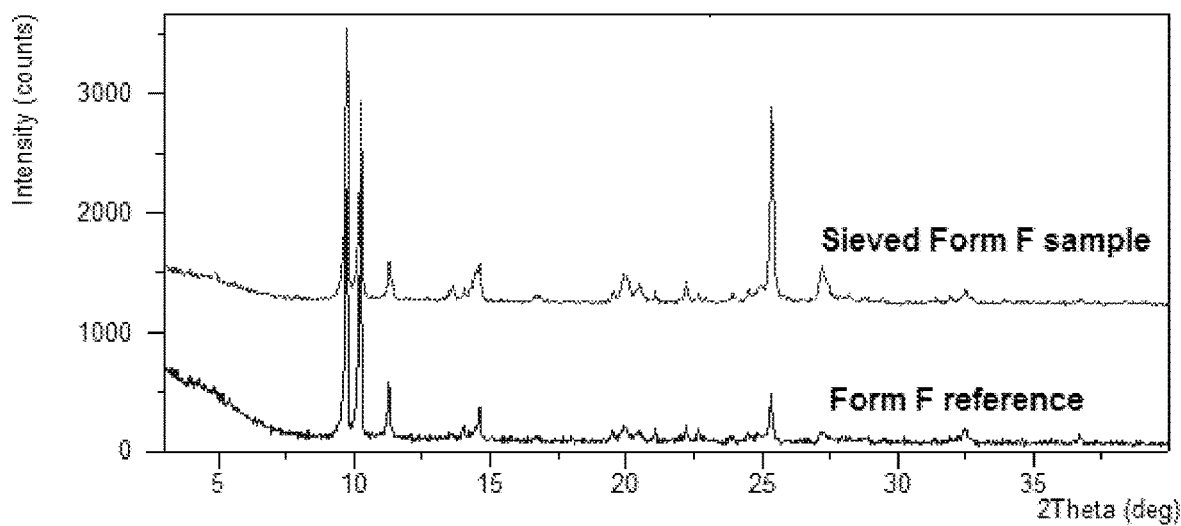
FIG. 20 shows an overlay of the X-ray diffraction diagrams of the crystalline forms of sepiapterin Form F before and after a grinding and sieving process and confirms the stability thereof to grinding and sieving.
Figure 21:
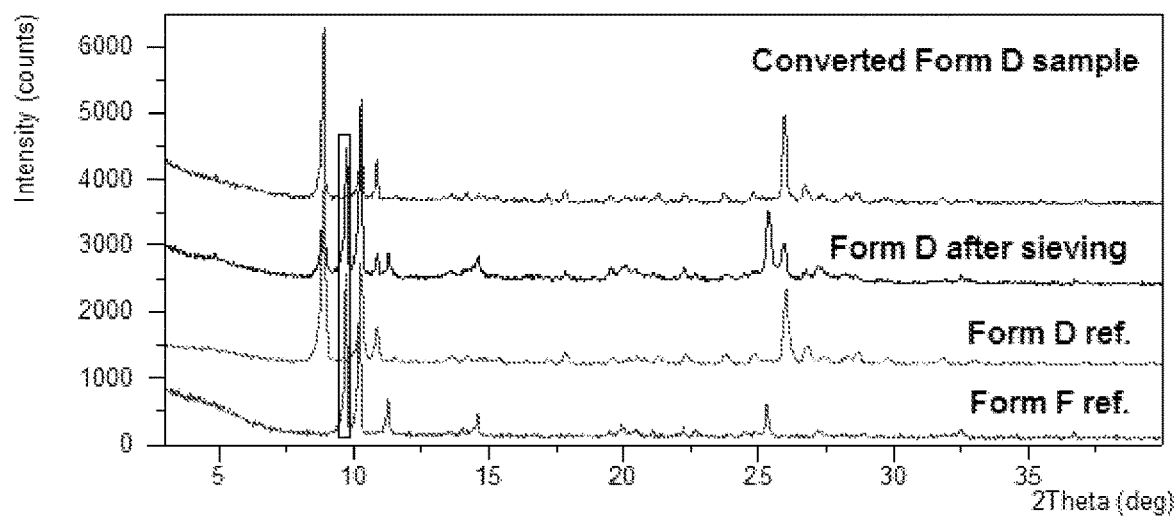
FIG. 21 shows an overlay of the X-ray diffraction diagrams of the crystalline forms of sepiapterin Form D before and after a grinding and sieving process along with sepiapterin Form D and Form F as references. This Figure demonstrates the potential instability of Form D to grinding and sieving.

FIG. 19 shows the X-ray diffraction diagram of Form A of sepiapterin free base. The most intense peak in the X-ray diffraction diagram is observed at an angle of refraction 2θ of about 7.4°. The crystalline Form A is characterized by the 2θ peak positions of at least about 4.7°, about 7.4°, about 9.5°, about 11.3°, about 15.6°, about 26.2°, and about 27.2°. In an essentially pure material, crystal Form A of sepiapterin free base, peaks can be observed at angles of refraction 2θ as set forth in Table 1.

TABLE 1

| Position [2θ°] | Relative Intensity |
|---|---|
| 4.7 | 47.76 |
| 7.4 | 100.00 |
| 9.5 | 33.54 |
| 11.3 | 19.31 |
| 12.4 | 8.49 |
| 13.4 | 3.60 |
| 14.2 | 8.24 |
| 15.6 | 15.08 |
| 16.4 | 11.97 |
| 17.6 | 8.35 |
| 18.4 | 5.03 |
| 19.8 | 9.18 |
| 21.5 | 5.44 |
| 24.4 | 5.56 |
| 26.2 | 35.37 |
| 27.2 | 19.11 |
| 28.9 | 5.93 |

The crystalline Form B of sepiapterin free base is characterized by peaks in the X-ray diffraction diagram observed at an angle of refraction 2θ of at least about 8.4, about 16.9, and about 25.4.

FIG. 1 shows the X-ray diffraction diagram of crystalline Form B of sepiapterin free base. The most intense peak in the X-ray diffraction diagram is observed at an angle of refraction 2θ of about 8.4°. The crystalline Form B is characterized by refractions at angles of refraction 2θ of at least about 8.4°, about 14.9°, about 16.9°, about 25.4°, and about 34.1°. In an essentially pure material of the crystal Form B of sepiapterin free base, peaks can be observed at angles of refraction 2θ as set forth in Table 2.

TABLE 2

| Position [2θ°] | Relative Intensity |
|---|---|
| 8.4 | 100.00 |
| 14.9 | 2.34 |
| 16.9 | 10.70 |
| 25.4 | 84.90 |
| 34.1 | 3.00 |

The crystalline Form C of sepiapterin free base is characterized by peaks in the X-ray diffraction diagram observed at an angle of refraction 2θ of at least at about 5.7°, about 7.8°, and about 25.4°.

Figure 2:
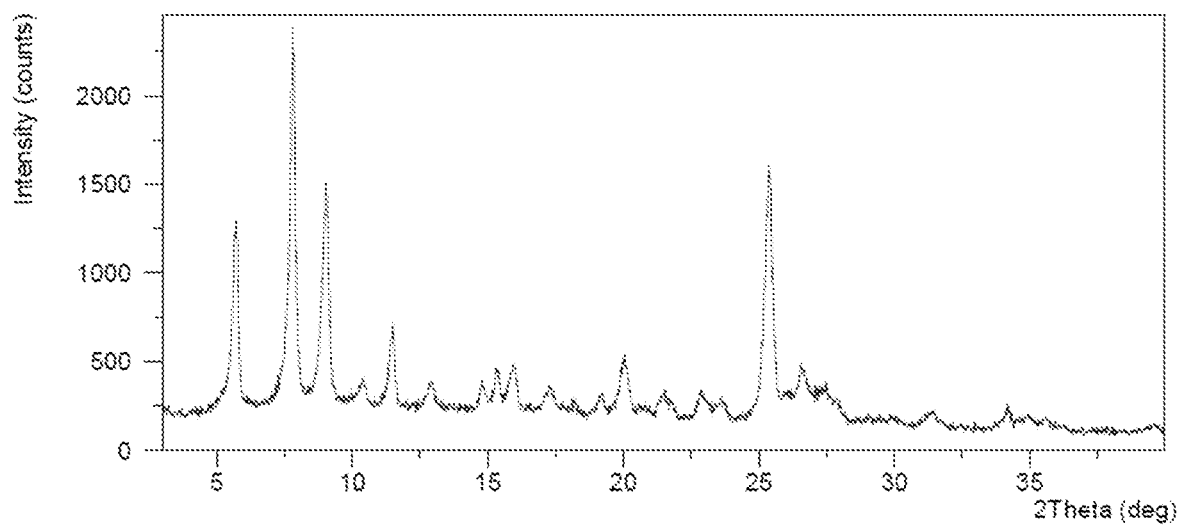
FIG. 2 shows the X-ray diffraction diagram of the crystalline Form C of sepiapterin free base.

FIG. 2 shows the X-ray diffraction diagram of crystalline Form C of sepiapterin free base. The most intense peak in the X-ray diffraction diagram is observed at an angle of refraction 2θ of at least about 7.8°. Crystalline Form C is characterized by refractions at angles of refraction 2θ of at least about 5.7°, about 7.8°, about 9.1°, about 11.5°, about 15.3°, about 16.0°, about 20.1°, about 25.4°, and about 26.6°. In an essentially pure material of Form C of sepiapterin free base, peaks can be observed at angles of refraction 2θ as set forth in Table 3.

TABLE 3

| Position [2θ°] | Relative Intensity |
|---|---|
| 5.7 | 48.91 |
| 7.8 | 100.00 |
| 9.1 | 59.49 |
| 10.4 | 8.72 |
| 11.5 | 24.53 |
| 12.9 | 8.50 |
| 14.8 | 9.24 |
| 15.3 | 12.53 |
| 16.0 | 14.09 |
| 17.2 | 7.22 |
| 18.2 | 4.25 |
| 19.2 | 5.78 |
| 20.1 | 14.54 |
| 21.5 | 6.47 |
| 22.9 | 6.85 |
| 23.7 | 4.80 |
| 25.4 | 65.68 |
| 26.6 | 14.53 |
| 27.4 | 8.39 |
| 31.5 | 3.74 |
| 34.2 | 4.36 |

The crystal Form D of sepiapterin free base is characterized by peaks in the X-ray diffraction diagram observed at least at an angle of refraction 2θ of about 8.9°, about 10.3°, and about 26.0°.

Figure 3:
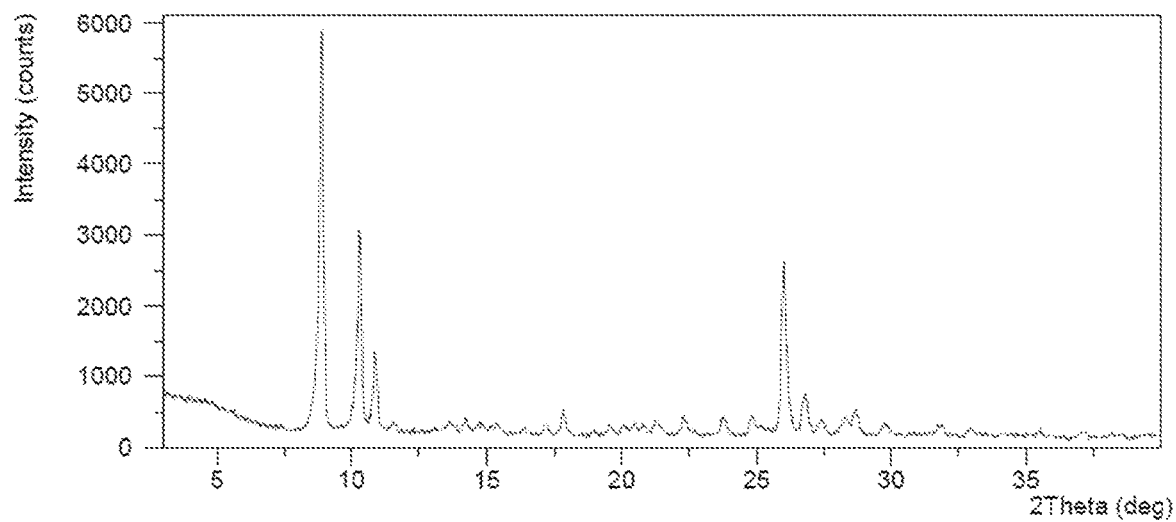
FIG. 3 shows the X-ray diffraction diagram of the crystalline Form D of sepiapterin free base.

FIG. 3 shows the X-ray diffraction diagram of crystal Form D of sepiapterin free base. The most intense peak in the X-ray diffraction diagram is observed at an angle of refraction 2θ of at least about 8.9°. The crystal Form D is characterized by refractions at angles of refraction 2θ of at least about 8.9°, about 10.3°, about 10.9°, about 17.8°, about 24.9°, about 26.0°, about 26.7°, about 26.8°, and about 28.3°. In an essentially pure material of Form D of sepiapterin free base, peaks can be observed at angles of refraction 2θ as set forth in Table 4.

TABLE 4

| Position [2θ°] | Relative Intensity |
|---|---|
| 8.9 | 100.00 |
| 10.3 | 49.92 |
| 10.9 | 19.96 |
| 11.6 | 2.15 |
| 13.6 | 2.99 |
| 14.2 | 3.45 |
| 14.8 | 2.35 |
| 15.4 | 2.59 |
| 16.4 | 1.55 |
| 17.2 | 2.33 |
| 17.8 | 6.24 |
| 19.6 | 2.62 |
| 20.1 | 2.28 |
| 20.5 | 3.09 |
| 20.8 | 2.27 |
| 21.3 | 3.60 |
| 22.3 | 4.79 |
| 23.7 | 4.31 |
| 24.9 | 5.19 |
| 26.0 | 41.94 |
| 26.7 | 8.58 |
| 26.8 | 9.17 |
| 27.4 | 3.98 |
| 28.3 | 4.75 |
| 28.7 | 6.60 |
| 29.8 | 3.03 |
| 31.8 | 2.72 |
| 33.0 | 2.03 |
| 35.5 | 1.57 |
| 37.1 | 1.09 |

The crystalline Form E of sepiapterin free base is characterized by an X-ray powder diffraction pattern obtained by irradiation with Cu Kα X-rays having peaks expressed as 2θ at least at about 6.0°, about 10.6°, about 12.1°, about 15.9°, about 20.8°, and about 24.6°.

Figure 22:
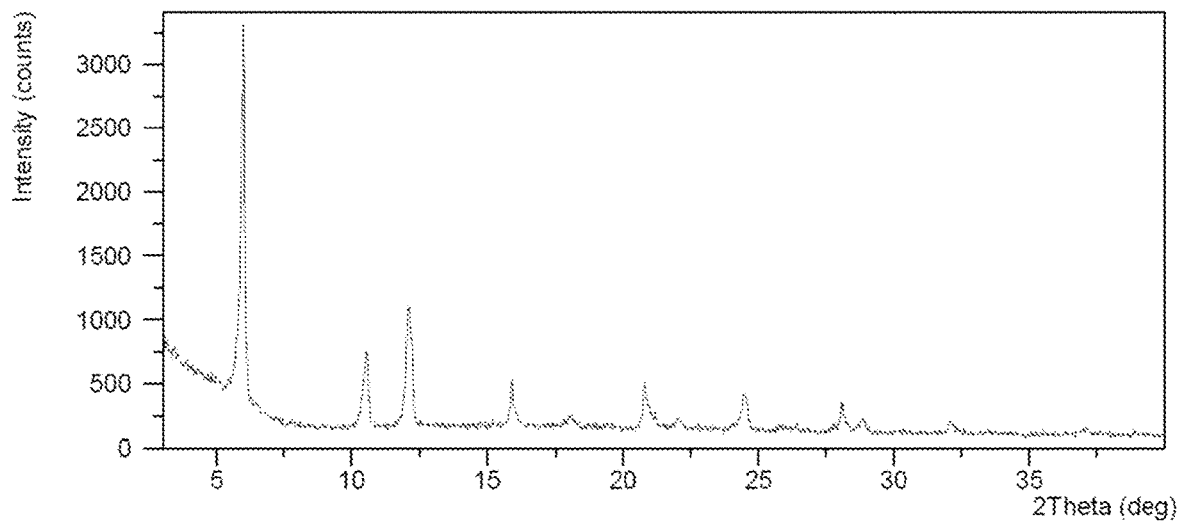
FIG. 22 shows the X-ray diffraction diagram of the crystalline Form E of sepiapterin free base.

FIG. 22 shows the X-ray diffraction diagram of Form E of sepiapterin free base. The most intense peak in the X-ray diffraction diagram is observed at an angle of refraction 2θ of at least about 6.0°. The crystalline Form E is characterized by refractions at angles of refraction 2θ of at least about 6.0°, about 10.6°, about 12.1°, about 15.9°, about 20.9°, and about 24.6°. In an essentially pure form, for crystalline Form E of sepiapterin free base, peaks can be observed at angles of refraction 2θ as set forth in Table 5.

TABLE 5

| Position [2θ°] | Relative Intensity |
|---|---|
| 6.0 | 100.00 |
| 10.6 | 20.78 |
| 12.1 | 31.95 |
| 15.9 | 12.83 |
| 18.1 | 3.39 |
| 20.9 | 11.63 |
| 22.1 | 2.79 |
| 24.6 | 8.28 |
| 26.1 | 0.88 |
| 28.1 | 7.33 |
| 28.9 | 3.77 |
| 32.1 | 3.57 |
| 37.0 | 1.03 |

The crystalline Form F of sepiapterin free base is characterized by peaks in the X-ray diffraction diagram observed at an angle of refraction 2θ of at least about 9.7°, about 10.2°, and about 11.3°.

Figure 4:
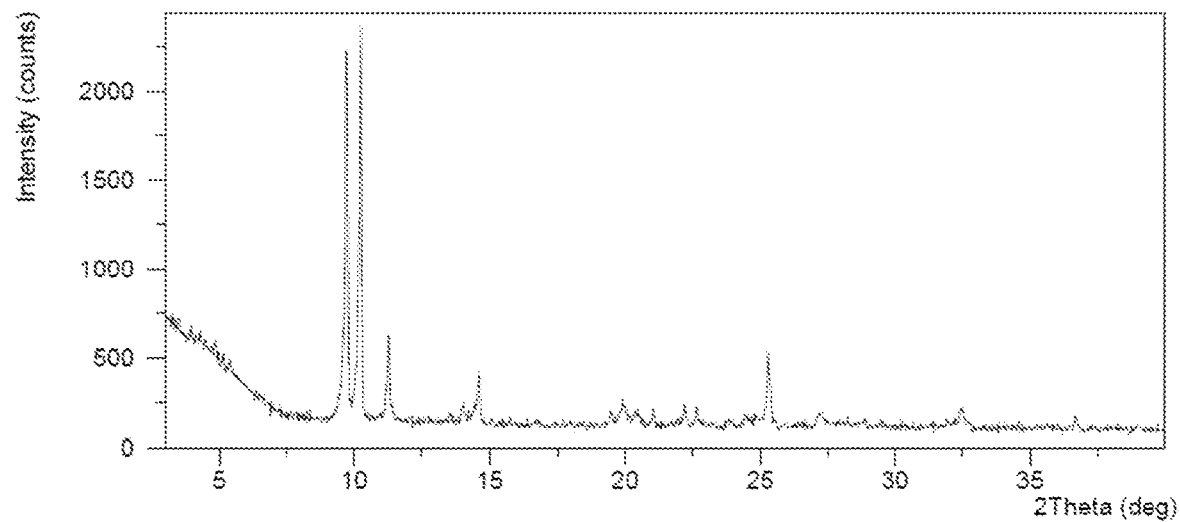
FIG. 4 shows the X-ray diffraction diagram of the crystalline Form F of sepiapterin free base.

FIG. 4 shows the X-ray diffraction diagram of the F form of sepiapterin free base. The most intense peak in the X-ray diffraction diagram is observed at an angle of refraction 2θ of at least about 10.2°. The F form is characterized by refractions at angles of refraction 2θ of at least about 9.7°, about 10.2°, about 11.3°, about 14.0°, about 14.6°, about 19.9°, about 22.2°, about 25.3°, and about 32.4°. In an essentially pure F form of sepiapterin free base, peaks can be observed at angles of refraction 2θ as set forth in Table 6.

TABLE 6

| Position [2θ°] | Relative Intensity |
|---|---|
| 9.7 | 98.27 |
| 10.2 | 100.00 |
| 11.3 | 22.47 |
| 14.0 | 5.01 |
| 14.6 | 12.36 |
| 19.9 | 5.63 |
| 21.1 | 3.72 |
| 22.2 | 5.37 |
| 22.7 | 4.04 |
| 24.5 | 2.99 |
| 25.3 | 17.65 |
| 27.2 | 3.10 |
| 32.4 | 5.29 |
| 36.7 | 2.72 |

Figure 5:
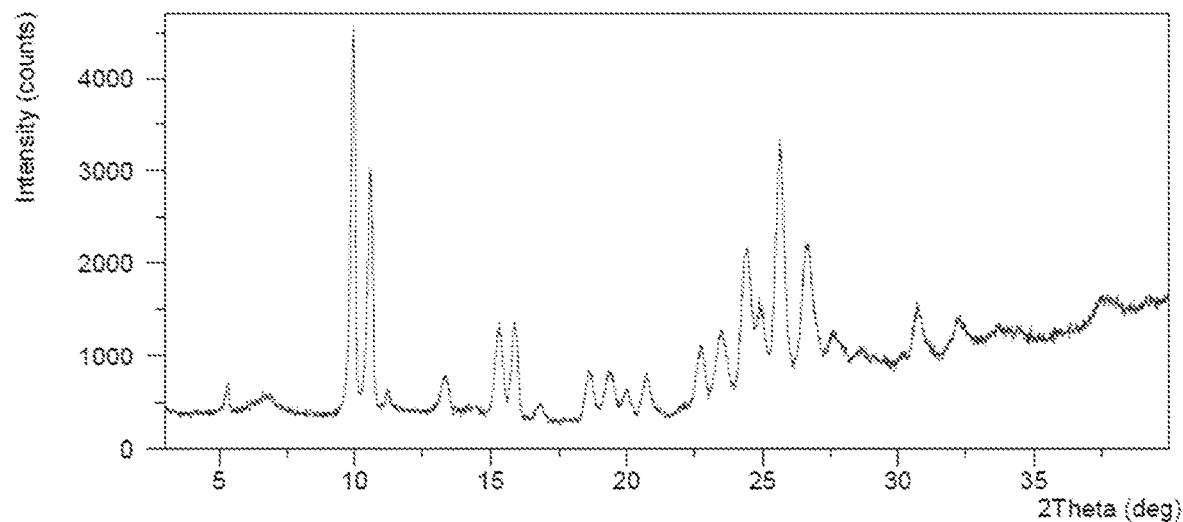
FIG. 5 shows the X-ray diffraction diagram of the crystalline Form G of sepiapterin free base.

The crystalline form G of sepiapterin free base is characterized by peaks in the X-ray diffraction diagram observed at an angle of refraction 2θ of at least about 10.0°, about 10.6°, and about 25.7°. FIG. 5 shows the X-ray diffraction diagram of the crystalline Form G of sepiapterin free base obtained at 120° C. The most intense peak in the X-ray diffraction diagram is observed at an angle of refraction 2θ of at least about 10.0°. More broadly, the G-crystal form is characterized by refractions at angles of refraction 2θ of at least about 10.0°, about 10.6°, about 11.2°, about 15.3°, about 15.9°, about 22.8°, about 24.4°, about 25.0°, about 25.7°, and about 26.6°. In an essentially pure material of the G-crystal form of sepiapterin free base, peaks can be observed at angles of refraction 2θ as set forth in Table 7.

TABLE 7

| Position [2θ°] | Relative Intensity |
|---|---|
| 5.3 | 8.30 |
| 6.9 | 4.54 |
| 10.0 | 100.00 |
| 10.6 | 69.64 |
| 11.2 | 6.59 |
| 13.5 | 7.52 |
| 15.3 | 26.59 |
| 15.9 | 26.43 |
| 16.0 | 23.41 |
| 16.9 | 4.28 |
| 18.6 | 13.02 |
| 19.3 | 11.90 |
| 20.1 | 7.22 |
| 20.8 | 11.01 |
| 22.8 | 16.77 |
| 23.5 | 19.60 |
| 24.4 | 41.45 |
| 25.0 | 23.99 |
| 25.7 | 65.40 |
| 26.6 | 39.64 |
| 27.6 | 13.04 |
| 28.7 | 6.55 |
| 30.8 | 14.76 |
| 32.2 | 9.63 |
| 33.7 | 5.16 |
| 37.5 | 5.80 |

In the context of stating that crystalline Form A of sepiapterin free base exhibits an X-ray diffraction diagram essentially as in FIG. 19, the term "essentially" means that at least the major peaks of the diagram depicted in FIG. 19, i.e., those having a relative peak intensity of more than 20%, especially more than 30%, as compared to the most intense peak in the diagram, have to be present.

Alternatively, or in addition, crystalline Form A of sepiapterin free base is characterized by a DSC curve showing endothermal peaks at 82.8° C. and 179.8° C.

In the context of stating that crystalline Form B of sepiapterin free base exhibits an X-ray diffraction diagram essentially as in FIG. 1, the term "essentially" means that at least the major peaks of the diagram depicted in FIG. 1, i.e. those having a relative peak intensity of more than 20%, especially more than 30%, as compared to the most intense peak in the diagram, have to be present.

Alternatively, or in addition, the crystalline Form B of sepiapterin free base is characterized by a DSC curve showing a melting event at 195.2° C.

In a preferred embodiment, an essentially pure crystalline Form B of sepiapterin free base shows the X-ray diffraction diagram indicated in FIG. 1.

In another preferred embodiment, crystalline Form B of sepiapterin free base shows an X-ray diffraction diagram of the type shown in FIG. 1, in which the relative peak intensities of each peak do not deviate by more than 10% from the relative peak intensities in the diagram shown in FIG. 1, especially an X-ray diffraction diagram identical to that shown in FIG. 1.

In the context of stating that crystalline Form C of sepiapterin free base exhibits an X-ray diffraction diagram essentially as in FIG. 2, the term "essentially" means that at least the major peaks of the diagram depicted in FIG. 2, i.e., those having a relative peak intensity of more than 20%, especially more than 30%, as compared to the most intense peak in the diagram, have to be present.

Alternatively, the crystalline Form C of sepiapterin free base is characterized by a DSC curve showing five endothermal peaks at 58.3° C., 101.8° C., 129.8° C., 156.5° C., and 168.3° C.

In one preferred embodiment, the essentially pure crystalline Form C of sepiapterin free base shows the X-ray diffraction diagram indicated in FIG. 2.

In another preferred embodiment, the crystalline Form C of sepiapterin free base shows an X-ray diffraction diagram of the type shown in FIG. 2, in which the relative peak intensities of each peak do not deviate by more than 10% from the relative peak intensities in the diagram shown in FIG. 2, especially an X-ray diffraction diagram identical to that shown in FIG. 2.

In the context of stating that crystalline Form D of sepiapterin free base exhibits an X-ray diffraction diagram essentially as in FIG. 3, the term "essentially" means that at least the major peaks of the diagram depicted in FIG. 3, i.e., those having a relative peak intensity of more than 20%, especially more than 30%, as compared to the most intense peak in the diagram, have to be present.

Alternatively, the crystalline Form D of sepiapterin free base is characterized by a DSC curve showing three endotherms at 42.7° C., 66.3° C., and 232.9° C.

In one preferred embodiment, the essentially pure crystalline Form D of sepiapterin free base shows the X-ray diffraction diagram indicated in FIG. 3.

In another preferred embodiment, the crystalline Form D of sepiapterin free base shows an X-ray diffraction diagram of the type shown in FIG. 3, in which the relative peak intensities of each peak do not deviate by more than 10% from the relative peak intensities in the diagram shown in FIG. 3, especially an X-ray diffraction diagram identical to that shown in FIG. 3.

In the context of stating that the crystalline Form E of sepiapterin free base exhibits an X-ray diffraction diagram essentially as in FIG. 22, the term "essentially" means that at least the major peaks of the diagram depicted in FIG. 22, i.e. those having a relative peak intensity of more than 20%, especially more than 30%, as compared to the most intense peak in the diagram, have to be present.

Alternatively, the crystalline Form E of sepiapterin free base is characterized by a DSC curve showing two endothermal peaks at 112.9° C. and 195.8° C.

In the context of stating that the crystalline Form F of sepiapterin free base exhibits an X-ray diffraction diagram essentially as in FIG. 4, the term "essentially" means that at least the major peaks of the diagram depicted in FIG. 4, i.e., those having a relative peak intensity of more than 20%, especially more than 30%, as compared to the most intense peak in the diagram, have to be present.

Alternatively, the crystalline Form F of sepiapterin free base is characterized by a DSC curve showing two endotherms at 71.6° C. and 233.4° C.

In one preferred embodiment, the essentially pure crystalline Form F of sepiapterin free base shows the X-ray diffraction diagram indicated in FIG. 4.

In another preferred embodiment, the crystalline Form F of sepiapterin free base shows an X-ray diffraction diagram of the type shown in FIG. 4, in which the relative peak intensities of each peak do not deviate by more than 10% from the relative peak intensities in the diagram shown in FIG. 4, especially an X-ray diffraction diagram identical to that shown in FIG. 4.

In the context of stating that the crystalline Form G of sepiapterin free base exhibits an X-ray diffraction diagram essentially as in FIG. 5, the term "essentially" means that at least the major peaks of the diagram depicted in FIG. 5, i.e., those having a relative peak intensity of more than 20%, especially more than 30%, as compared to the most intense peak in the diagram, have to be present.

In one preferred embodiment, the essentially pure crystalline Form G of sepiapterin free base shows the X-ray diffraction diagram indicated in FIG. 5.

In another preferred embodiment, the crystalline Form G of sepiapterin free base shows an X-ray diffraction diagram of the type shown in FIG. 5, in which the relative peak intensities of each peak do not deviate by more than 10% from the relative peak intensities in the diagram shown in FIG. 5, especially an X-ray diffraction diagram identical to that shown in FIG. 5.

The invention also provides a crystalline form of sepiapterin hydrochloride salt.

In an embodiment, the crystalline hydrochloride salt is characterized by an X-ray powder diffraction pattern obtained by irradiation with Cu Kα X-rays having peaks expressed as 2θ at least at about 7.8°, about 12.9°, and about 26.2°.

The invention further provides a crystalline polymorph form of a salt of sepiapterin. In certain embodiments, the invention provides a crystalline polymorph form of a salt of sepiapterin, wherein the salt is a salt of sepiapterin with sulfuric acid, p-toluene sulfonic acid, methane sulfonic acid, benzene sulfonic acid, malonic acid, tartaric acid (e.g., L-tartaric acid), phosphoric acid, gentisic acid, fumaric acid, glycolic acid, acetic acid, or nicotinic acid.

In particular embodiments, the crystalline polymorph salt is selected from the group consisting of:

crystalline Form 1 methanesulfonate salt characterized by an X-ray powder diffraction pattern obtained by irradiation with Cu Kα X-rays having peaks expressed as 2θ at least at about 7.8°, about 23.5°, and about 29.0°;

crystalline Form 2 methanesulfonate salt characterized by an X-ray powder diffraction pattern obtained by irradiation with Cu Kα X-rays having peaks expressed as 2θ at least at about 7.9°, about 23.4°, and about 28.9°;

crystalline Form 3 methanesulfonate salt characterized by an X-ray powder diffraction pattern obtained by irradiation with Cu Kα X-rays having peaks expressed as 2θ at least at about 21.7°, about 26.0°, and about 28.9°;

crystalline nicotinate salt characterized by an X-ray powder diffraction pattern obtained by irradiation with Cu Kα X-rays having peaks expressed as 2θ at least at about 9.5°, about 9.9°, and about 24.5°;

crystalline p-toluenesulfonate salt characterized by an X-ray powder diffraction pattern obtained by irradiation with Cu Kα X-rays having peaks expressed as 2θ at least at about 6.5°, about 15.1°, and about 23.4°;

crystalline benzenesulfonate salt characterized by an X-ray powder diffraction pattern obtained by irradiation with Cu Kα X-rays having peaks expressed as 2θ at least at about 6.5°, about 14.8°, and about 19.6°;

crystalline phosphate salt characterized by an X-ray powder diffraction pattern obtained by irradiation with Cu Kα X-rays having peaks expressed as 2θ at least at about 16.6°, about 22.2°, and about 25.6°;

crystalline malonate salt characterized by an X-ray powder diffraction pattern obtained by irradiation with Cu Kα X-rays having peaks expressed as 2θ at least at about 6.9°, about 22.7°, and about 23.8°;

crystalline tartrate salt characterized by an X-ray powder diffraction pattern obtained by irradiation with Cu Kα X-rays having peaks expressed as 2θ at least at about 7.3°, about 14.2°, and about 21.8°;

crystalline gentisate salt characterized by an X-ray powder diffraction pattern obtained by irradiation with Cu Kα X-rays having peaks expressed as 2θ at least at about 7.1°, about 8.7°, and about 26.7°;

crystalline fumarate salt characterized by an X-ray powder diffraction pattern obtained by irradiation with Cu Kα X-rays having peaks expressed as 2θ at about 11.3°, about 24.0°, and about 28.2°;

crystalline glycolate salt characterized by an X-ray powder diffraction pattern obtained by irradiation with Cu Kα X-rays having peaks expressed as 2θ at least at about 7.6°, about 10.7°, and about 24.0°;

crystalline acetate salt characterized by an X-ray powder diffraction pattern obtained by irradiation with Cu Kα X-rays having peaks expressed as 2θ at least at about 6.2°, about 12.0°, and about 18.1';

crystalline Form 1 sulfate salt characterized by an X-ray powder diffraction pattern obtained by irradiation with Cu Kα X-rays having peaks expressed as 2θ at least at about 5.1°, about 7.8°, and about 23.0°; and crystalline Form 2 sulfate salt characterized by an X-ray powder diffraction pattern obtained by irradiation with Cu Kα X-rays having peaks expressed as 2θ at least at about 7.8°, about 8.8°, and about 24.1°.

The crystalline hydrochloride salt of sepiapterin free base is characterized by peaks in the X-ray diffraction diagram observed at an angle of refraction 2θ of at least about 7.8°, about 12.9°, and about 26.2°.

Figure 6:
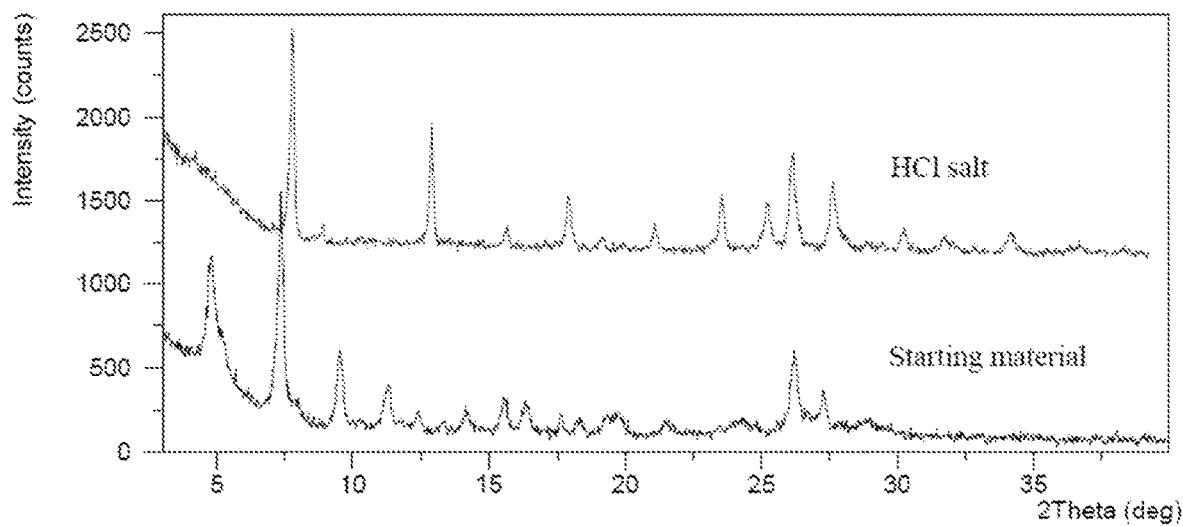
FIG. 6 shows an overlay of the X-ray diffraction diagrams of the crystalline Form 1 hydrochloride salt of sepiapterin and of the starting sepiapterin free base used in the preparation of the hydrochloride salt.

FIG. 6 shows the X-ray diffraction diagram of the crystalline hydrochloride salt of sepiapterin free base. The most intense peak in the X-ray diffraction diagram is observed at an angle of refraction 2θ of at least about 7.8°. In an essentially pure material of the crystalline hydrochloride salt of sepiapterin free base, peaks can be observed at angles of refraction 2θ as set forth in Table 8.

TABLE 8

| Position [2θ°] | Relative Intensity |
|---|---|
| 7.8 | 100.00 |
| 8.9 | 6.89 |
| 12.9 | 58.56 |
| 15.6 | 8.52 |
| 17.9 | 25.23 |
| 19.2 | 5.48 |
| 21.1 | 10.97 |
| 23.6 | 25.15 |
| 25.2 | 22.66 |
| 26.2 | 45.91 |
| 27.6 | 32.94 |
| 30.3 | 10.50 |
| 31.7 | 7.83 |
| 34.2 | 8.87 |
| 36.7 | 3.67 |

The crystalline Form 1 methanesulfonate salt of sepiapterin free base is characterized by peaks in the X-ray diffraction diagram observed at an angle of refraction 2θ at least at about 7.8°, about 23.5°, and about 29.0°.

Figure 7:
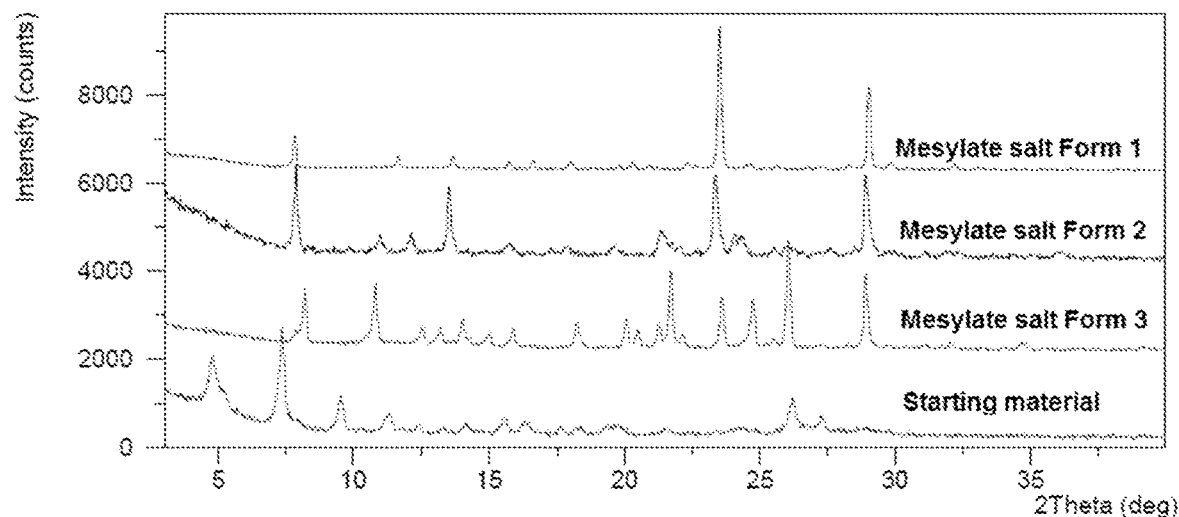
FIG. 7 shows an overlay of the X-ray diffraction diagrams of the crystalline Form 1 methanesulfonate salt, of Form 2 methanesulfonate salt, of Form 3 methanesulfonate salts of sepiapterin and of the starting sepiapterin free base used in the preparation of the methanesulfonate salts.

FIG. 7 shows the X-ray diffraction diagram of the crystalline Form 1 methanesulfonate salt of sepiapterin free base. The most intense peak in the X-ray diffraction diagram is observed at an angle of refraction 2θ of at least about 23.5°. In an essentially pure material of the crystalline Form 1 methanesulfonate salt of sepiapterin free base, peaks can be observed at angles of refraction 2θ as set forth in Table 9.

TABLE 9

| Position [2θ°] | Relative Intensity |
|---|---|
| 7.9 | 21.77 |
| 11.7 | 8.20 |
| 13.7 | 8.52 |
| 15.7 | 4.79 |
| 16.6 | 5.34 |
| 18.0 | 5.66 |
| 19.8 | 2.10 |
| 20.3 | 5.36 |
| 20.9 | 2.43 |
| 22.3 | 4.25 |
| 22.7 | 2.15 |
| 23.5 | 100.00 |
| 24.7 | 3.69 |
| 25.6 | 2.70 |
| 26.8 | 1.79 |
| 27.2 | 1.68 |
| 28.3 | 2.75 |
| 29.0 | 57.60 |
| 29.8 | 5.18 |
| 30.5 | 1.37 |
| 32.2 | 4.66 |
| 33.0 | 1.64 |
| 36.5 | 1.29 |

The crystalline Form 2 methanesulfonate salt of sepiapterin free base is characterized by peaks in the X-ray diffraction diagram observed at an angle of refraction 2θ at least at about 7.9°, about 23.4°, and about 28.9°.

FIG. 7 shows the X-ray diffraction diagram of the crystalline Form 2 methanesulfonate salt of sepiapterin free base. The most intense peak in the X-ray diffraction diagram is observed at an angle of refraction 2θ of at least about 23.5°. In an essentially pure material of the crystalline Form 2 methanesulfonate salt of sepiapterin free base, peaks can be observed at angles of refraction 2θ as set forth in Table 10.

TABLE 10

| Position [2θ°] | Relative Intensity |
| --- | --- |
| 7.9 | 100.00 |
| 11.0 | 21.32 |
| 12.1 | 22.02 |
| 13.5 | 79.87 |
| 15.7 | 11.87 |
| 17.8 | 9.81 |
| 19.7 | 10.93 |
| 21.3 | 26.79 |
| 23.4 | 96.13 |
| 24.1 | 24.88 |
| 24.3 | 22.10 |
| 25.5 | 9.45 |
| 26.0 | 11.27 |
| 27.6 | 7.63 |
| 28.9 | 95.64 |
| 31.2 | 4.39 |
| 36.1 | 6.65 |

The crystalline Form 3 methanesulfonate salt of sepiapterin free base is characterized by peaks in the X-ray diffraction diagram observed at an angle of refraction 2θ at least at about 21.7°, about 26.0°, and about 28.9°.

FIG. 7 shows the X-ray diffraction diagram of the crystalline Form 3 methanesulfonate salt of sepiapterin free base. The most intense peak in the X-ray diffraction diagram is observed at an angle of refraction 2θ of at least about 26.0°. In an essentially pure material of the crystalline Form 3 methanesulfonate salt of sepiapterin free base, peaks can be observed at angles of refraction 2θ as set forth in Table 11.

TABLE 11

| Position [2θ°] | Relative Intensity |
| --- | --- |
| 8.2 | 47.29 |
| 10.8 | 56.14 |
| 12.6 | 16.34 |
| 13.2 | 15.90 |
| 14.0 | 24.39 |
| 15.0 | 12.03 |
| 15.9 | 16.20 |
| 18.2 | 22.97 |
| 20.1 | 25.53 |
| 20.5 | 14.97 |
| 21.3 | 22.70 |
| 21.7 | 71.48 |
| 22.2 | 11.40 |
| 23.6 | 46.37 |
| 24.8 | 44.00 |
| 25.5 | 9.08 |
| 26.1 | 100.00 |
| 27.3 | 3.52 |
| 28.9 | 68.42 |
| 31.2 | 4.49 |
| 32.1 | 6.48 |
| 34.8 | 5.95 |
| 35.6 | 1.67 |
| 39.1 | 2.91 |

The crystalline nicotinate salt of sepiapterin free base is characterized by peaks in the X-ray diffraction diagram observed at an angle of refraction 2θ at least at about 9.5°, about 9.9°, and about 24.5°.

Figure 8:
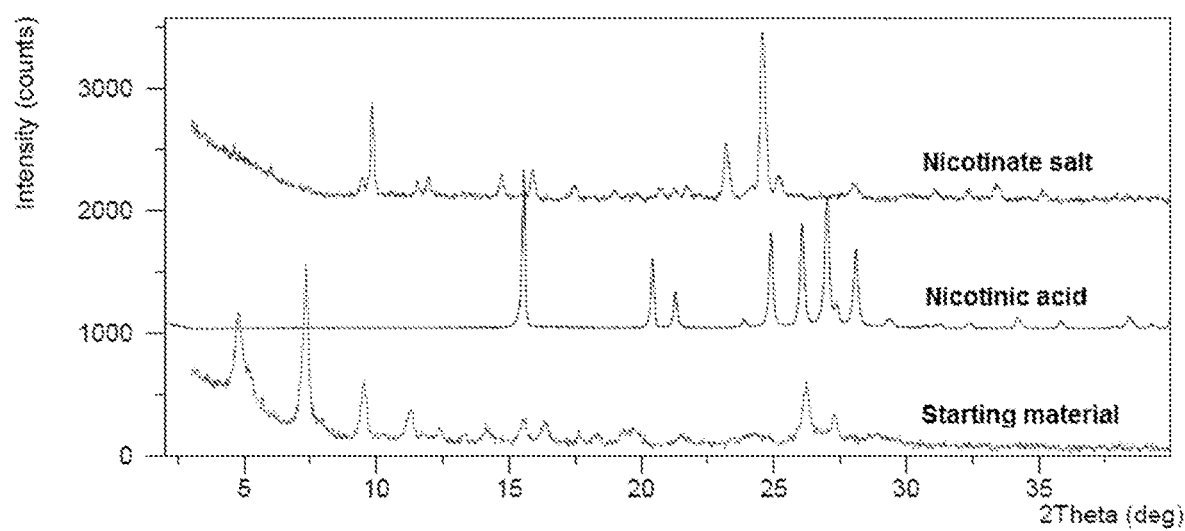
FIG. 8 shows an overlay of the X-ray diffraction diagrams of the crystalline nicotinate salt of sepiapterin, of nicotinic acid, and of the starting sepiapterin free base used in the preparation of the nicotinate salt.

FIG. 8 shows the X-ray diffraction diagram of the crystalline nicotinate salt of sepiapterin free base. The most intense peak in the X-ray diffraction diagram is observed at an angle of refraction 2θ of at least about 24.5°. In an essentially pure material of the crystalline nicotinate salt of sepiapterin free base, peaks can be observed at angles of refraction 2θ as set forth in Table 12.

TABLE 12

| Position [2θ°] | Relative Intensity |
| --- | --- |
| 9.5 | 10.29 |
| 9.9 | 53.95 |
| 11.5 | 9.31 |
| 12.0 | 11.76 |
| 14.7 | 14.20 |
| 15.9 | 17.61 |
| 17.5 | 7.53 |
| 19.0 | 5.37 |
| 20.8 | 5.88 |
| 21.3 | 6.12 |
| 21.7 | 7.20 |
| 23.2 | 34.05 |
| 24.5 | 100.00 |
| 25.2 | 12.90 |
| 28.0 | 8.51 |
| 31.1 | 5.39 |
| 32.3 | 4.52 |
| 33.4 | 8.02 |
| 35.1 | 5.05 |

The crystalline p-toluenesulfonate salt of sepiapterin free base is characterized by peaks in the X-ray diffraction diagram observed at an angle of refraction 2θ at least at about 6.5°, about 15.1°, and about 23.4°.

Figure 9:
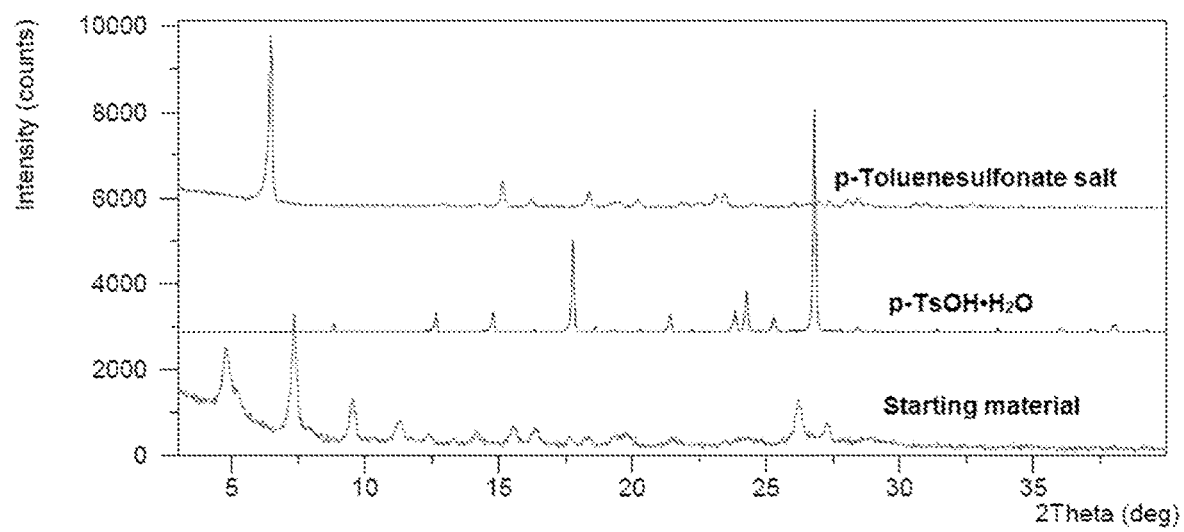
FIG. 9 shows an overlay of the X-ray diffraction diagrams of the crystalline p-toluenesulfonate salt of sepiapterin, of p-toluene sulfonic acid, and of the starting sepiapterin free base used in the preparation of the p-toluenesulfonate salt.

FIG. 9 shows the X-ray diffraction diagram of the crystalline p-toluenesulfonate salt of sepiapterin free base. The most intense peak in the X-ray diffraction diagram is observed at an angle of refraction 2θ of at least about 6.5°. In an essentially pure material of the p-toluenesulfonate salt of sepiapterin free base, peaks can be observed at angles of refraction 2θ as set forth in Table 13.

TABLE 13

| Position [2θ°] | Relative Intensity |
| --- | --- |
| 6.5 | 100.00 |
| 12.9 | 1.79 |
| 14.3 | 1.39 |
| 15.1 | 15.36 |
| 16.2 | 5.33 |
| 18.4 | 8.96 |
| 19.6 | 3.06 |
| 20.2 | 4.86 |
| 21.8 | 2.23 |
| 22.5 | 2.95 |
| 23.1 | 7.99 |
| 23.4 | 9.14 |
| 24.5 | 1.81 |
| 26.0 | 2.48 |
| 27.0 | 4.49 |
| 27.3 | 3.93 |
| 28.1 | 5.31 |
| 28.4 | 5.59 |
| 28.8 | 2.05 |
| 30.6 | 2.24 |
| 31.0 | 1.98 |
| 32.6 | 1.82 |

The crystalline benzenesulfonate salt of sepiapterin free base is characterized by peaks in the X-ray diffraction diagram observed at an angle of refraction 2θ at least at about 6.5°, about 14.8°, and about 19.6°.

Figure 10:
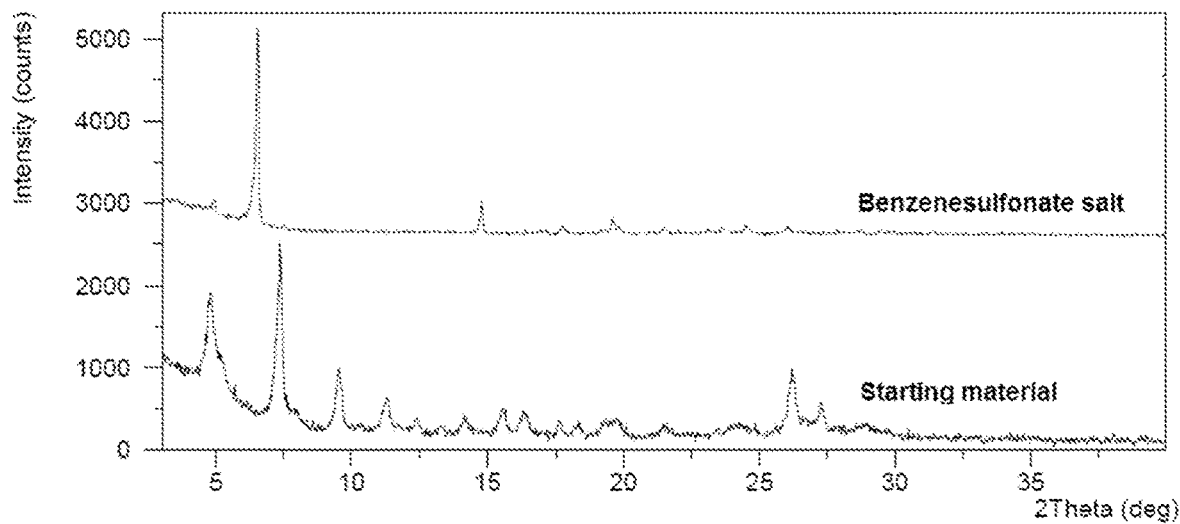
FIG. 10 shows an overlay of the X-ray diffraction diagrams of the crystalline benzenesulfonate salt of sepiapterin, of benzene sulfonic acid, and of the starting sepiapterin free base used in the preparation of the benzenesulfonate salt.

FIG. 10 shows the X-ray diffraction diagram of the crystalline benzenesulfonate salt of sepiapterin free base. The most intense peak in the X-ray diffraction diagram is observed at an angle of refraction 2θ of at least about 6.5°. In an essentially pure material of the benzenesulfonate salt of sepiapterin free base, peaks can be observed at angles of refraction 2θ as set forth in Table 14.

TABLE 14

| Position [2θ°] | Relative Intensity |
|---|---|
| 4.9 | 5.90 |
| 6.5 | 100.00 |
| 14.8 | 16.73 |
| 17.8 | 4.23 |
| 19.6 | 7.98 |
| 21.5 | 2.49 |
| 23.7 | 3.46 |
| 24.5 | 3.84 |
| 26.1 | 3.29 |

The crystalline phosphate salt of sepiapterin free base is characterized by peaks in the X-ray diffraction diagram observed at an angle of refraction 2θ at least at about 16.6°, about 22.2°, and about 25.6°.

Figure 11:
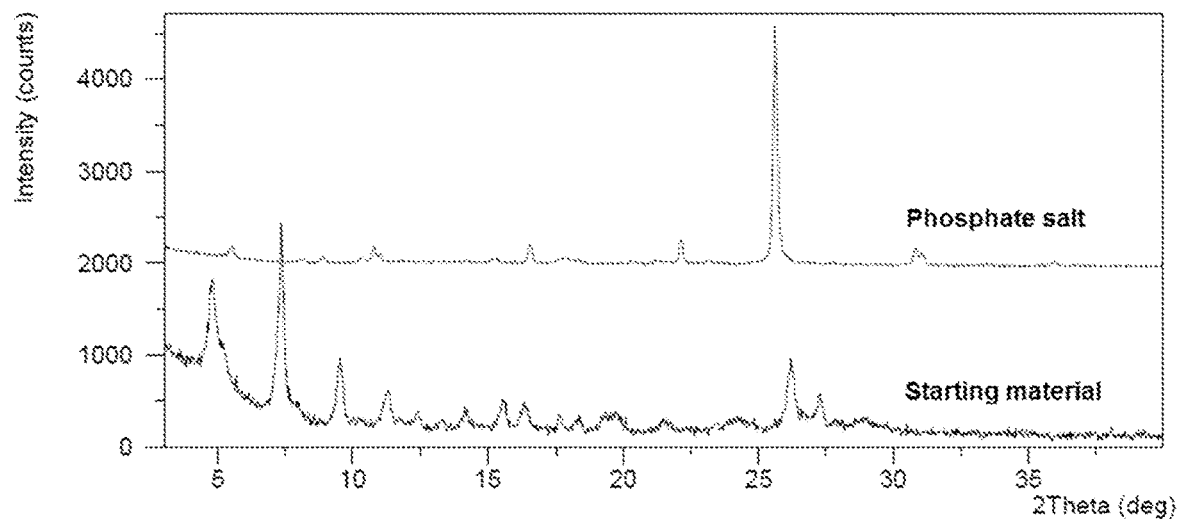
FIG. 11 shows an overlay of the X-ray diffraction diagrams of the crystalline phosphate salt of sepiapterin and of the starting sepiapterin free base used in the preparation of the phosphate salt.

FIG. 11 shows the X-ray diffraction diagram of the crystalline phosphate salt of sepiapterin free base. The most intense peak in the X-ray diffraction diagram is observed at an angle of refraction 2θ of at least about 25.6°. In an essentially pure material of the crystalline phosphate salt of sepiapterin free base, peaks can be observed at angles of refraction 2θ as set forth in Table 15.

TABLE 15

| Position [2θ°] | Relative Intensity |
|---|---|
| 5.5 | 4.41 |
| 8.1 | 1.21 |
| 8.9 | 2.21 |
| 10.3 | 1.79 |
| 10.8 | 5.80 |
| 15.3 | 1.84 |
| 16.6 | 8.35 |
| 17.7 | 1.95 |
| 20.3 | 1.40 |
| 21.2 | 1.61 |
| 22.2 | 9.77 |
| 23.1 | 1.74 |
| 25.6 | 100.00 |
| 30.8 | 6.31 |
| 31.1 | 4.85 |
| 33.5 | 0.73 |
| 36.0 | 1.70 |

The crystalline malonate salt of sepiapterin free base is characterized by peaks in the X-ray diffraction diagram observed at an angle of refraction 2θ at least at about 6.9°, about 22.7°, and about 23.8°.

Figure 12:
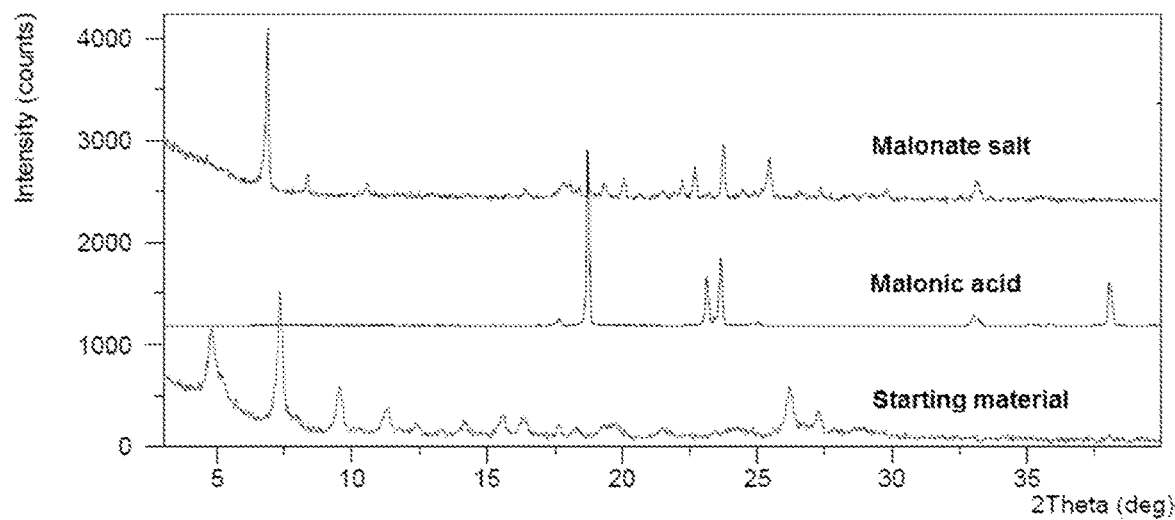
FIG. 12 shows an overlay of the X-ray diffraction diagrams of the crystalline malonate salt of sepiapterin, of malonic acid, and of the starting sepiapterin free base used in the preparation of the malonate salt.

FIG. 12 shows the X-ray diffraction diagram of the crystalline malonate salt of sepiapterin free base. The most intense peak in the X-ray diffraction diagram is observed at an angle of refraction 2θ of at least about 6.9°. In an essentially pure material of the crystalline malonate salt of sepiapterin free base, peaks can be observed at angles of refraction 2θ as set forth in Table 16.

TABLE 16

| Position [2θ°] | Relative Intensity |
|---|---|
| 6.9 | 100.00 |
| 8.4 | 13.11 |
| 10.6 | 7.62 |
| 16.4 | 5.63 |
| 17.8 | 9.73 |
| 19.3 | 8.96 |

TABLE 16-continued

| Position [2θ°] | Relative Intensity |
|---|---|
| 20.1 | 9.99 |
| 22.2 | 10.50 |
| 22.7 | 20.52 |
| 23.8 | 34.02 |
| 24.5 | 5.82 |
| 25.5 | 24.50 |
| 26.6 | 4.00 |
| 27.3 | 6.96 |
| 29.8 | 5.38 |
| 33.1 | 12.08 |

The crystalline L-tartrate salt of sepiapterin free base is characterized by peaks in the X-ray diffraction diagram observed at an angle of refraction 2θ at least at about 7.3°, about 14.2°, and about 21.8°.

Figure 13:
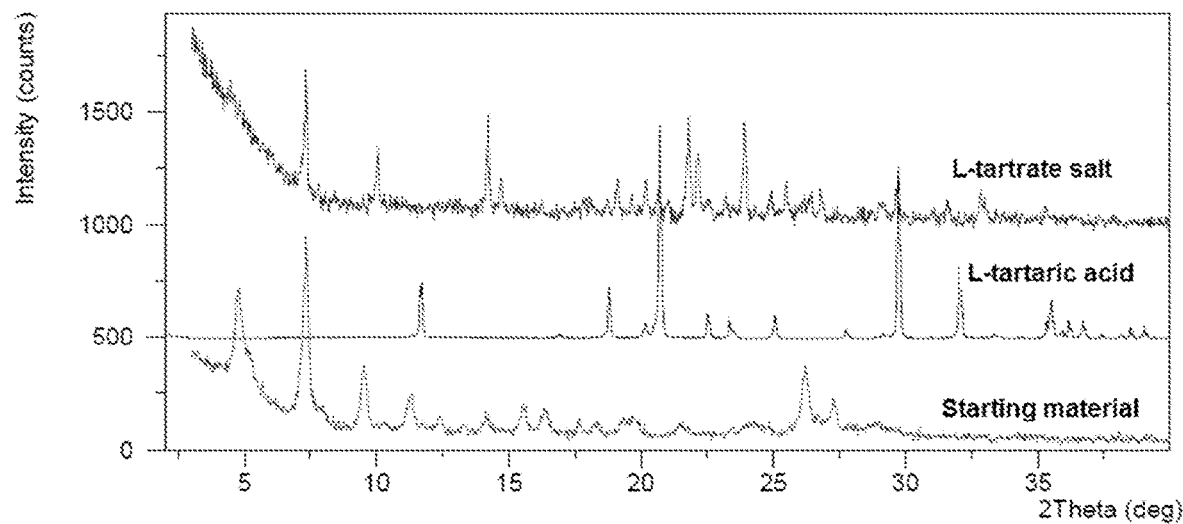
FIG. 13 shows an overlay of the X-ray diffraction diagrams of the crystalline L-tartrate salt of sepiapterin, of L-tartaric acid, and of the starting sepiapterin free base used in the preparation of the L-tartrate salt.

FIG. 13 shows the X-ray diffraction diagram of the crystalline L-tartrate salt of sepiapterin free base. The most intense peak in the X-ray diffraction diagram is observed at an angle of refraction 2θ of at least about 6.9°. In an essentially pure material of the crystalline L-tartrate salt of sepiapterin free base, peaks can be observed at angles of refraction 2θ as set forth in Table 17.

TABLE 17

| Position [2θ°] | Relative Intensity |
|---|---|
| 7.4 | 100.00 |
| 10.1 | 47.99 |
| 14.2 | 82.76 |
| 14.7 | 27.06 |
| 19.1 | 21.16 |
| 20.2 | 29.91 |
| 21.8 | 85.30 |
| 22.1 | 53.68 |
| 23.9 | 85.30 |
| 24.9 | 19.26 |
| 25.5 | 28.45 |
| 26.8 | 18.58 |
| 29.7 | 21.59 |
| 31.6 | 10.10 |
| 32.9 | 22.18 |

The crystalline gentisate salt of sepiapterin free base is characterized by peaks in the X-ray diffraction diagram observed at an angle of refraction 2θ at least at about 7.1°, about 8.7°, and about 26.7°.

Figure 14:
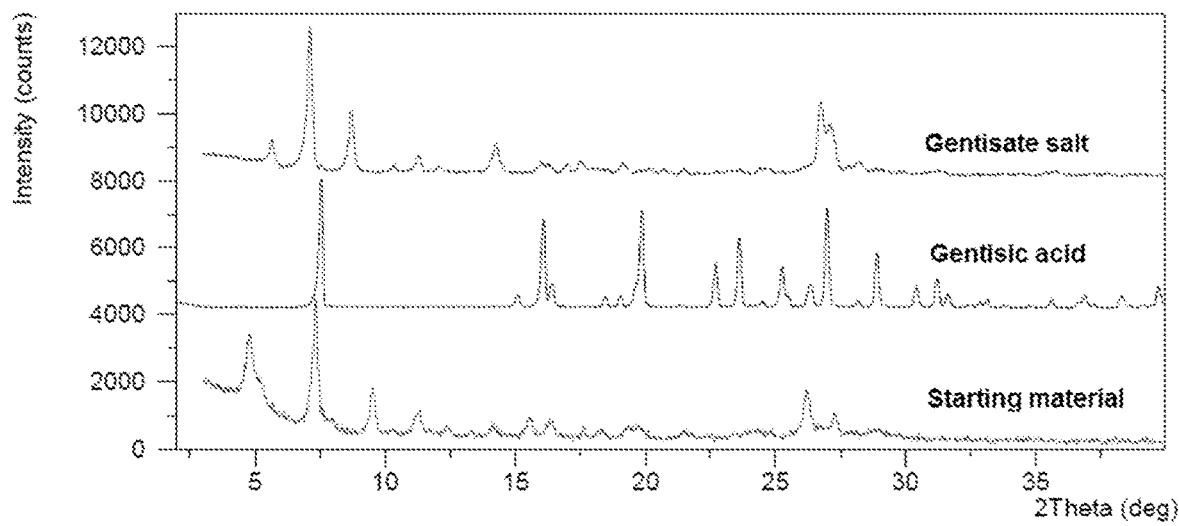
FIG. 14 shows an overlay of the X-ray diffraction diagrams of the crystalline gentisate salt of sepiapterin, of gentisic acid, and of the starting sepiapterin free base used in the preparation of the gentisate salt.

FIG. 14 shows the X-ray diffraction diagram of the crystalline gentisate salt of sepiapterin free base. The most intense peak in the X-ray diffraction diagram is observed at an angle of refraction 2θ of at least about 7.1°. In an essentially pure material of the crystalline gentisate salt of sepiapterin free base, peaks can be observed at angles of refraction 2θ as set forth in Table 18.

TABLE 18

| Position [2θ°] | Relative Intensity |
|---|---|
| 5.7 | 17.29 |
| 7.1 | 100.00 |
| 8.7 | 42.69 |
| 10.4 | 3.94 |
| 11.3 | 11.69 |
| 12.1 | 4.13 |
| 14.3 | 21.10 |
| 16.0 | 6.46 |
| 16.4 | 5.94 |
| 17.0 | 5.85 |
| 17.6 | 7.93 |

TABLE 18-continued

| Position [2θ°] | Relative Intensity |
|---|---|
| 19.1 | 8.27 |
| 20.20 | 3.47 |
| 20.7 | 2.90 |
| 21.5 | 3.37 |
| 23.6 | 2.69 |
| 24.4 | 4.50 |
| 26.7 | 52.20 |
| 27.1 | 35.49 |
| 28.2 | 8.74 |
| 28.9 | 4.31 |
| 29.9 | 2.62 |
| 31.4 | 2.99 |
| 34.4 | 1.28 |
| 35.8 | 3.54 |
| 37.6 | 0.57 |

The crystalline fumarate salt of sepiapterin free base is characterized by peaks in the X-ray diffraction diagram observed at an angle of refraction 2θ at least at about 11.3°, about 24.0°, and about 28.2°.

Figure 15:
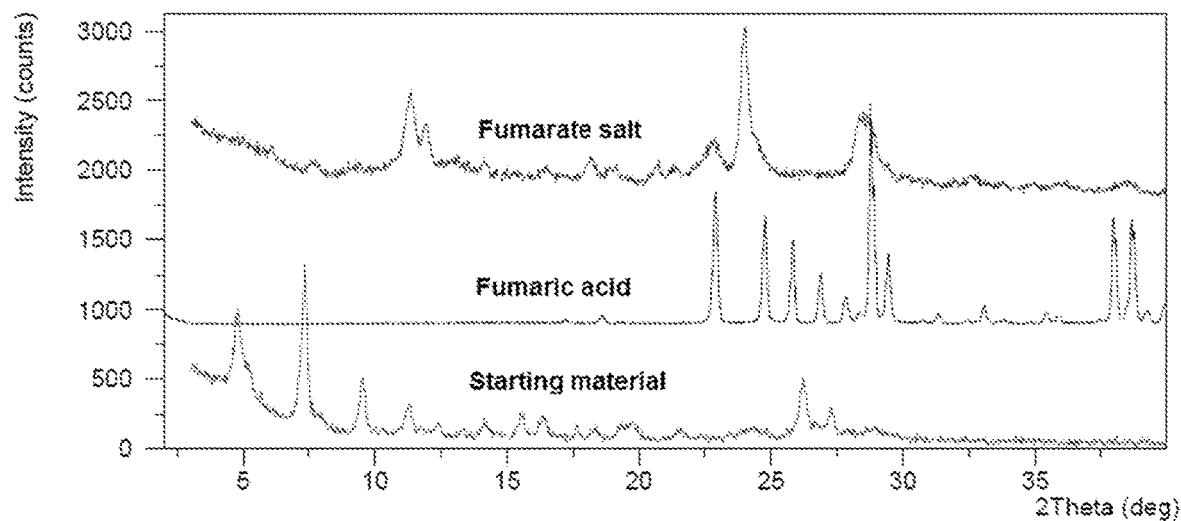
FIG. 15 shows an overlay of the X-ray diffraction diagrams of the crystalline fumarate salt of sepiapterin, of fumaric acid, and of the starting sepiapterin free base used in the preparation of the fumarate salt.

FIG. 15 shows the X-ray diffraction diagram of the crystalline fumarate salt of sepiapterin free base. The most intense peak in the X-ray diffraction diagram is observed at an angle of refraction 2θ of at least about 24.0°. In an essentially pure material of the crystalline fumarate salt of sepiapterin free base, peaks can be observed at angles of refraction 2θ as set forth in Table 19.

TABLE 19

| Position [2θ°] | Relative Intensity |
|---|---|
| 6.1 | 6.43 |
| 7.7 | 5.40 |
| 11.4 | 53.62 |
| 11.9 | 33.37 |
| 14.2 | 8.03 |
| 16.5 | 6.70 |
| 18.3 | 13.86 |
| 19.0 | 6.68 |
| 20.7 | 10.02 |
| 21.3 | 7.02 |
| 22.8 | 24.68 |
| 24.0 | 100.00 |
| 28.3 | 33.26 |
| 32.7 | 6.35 |
| 36.0 | 3.28 |
| 38.5 | 6.02 |

The crystalline glycolate salt of sepiapterin free base is characterized by peaks in the X-ray diffraction diagram observed at an angle of refraction 2θ at least at about 7.6°, about 10.7°, and about 24.0°.

Figure 16:
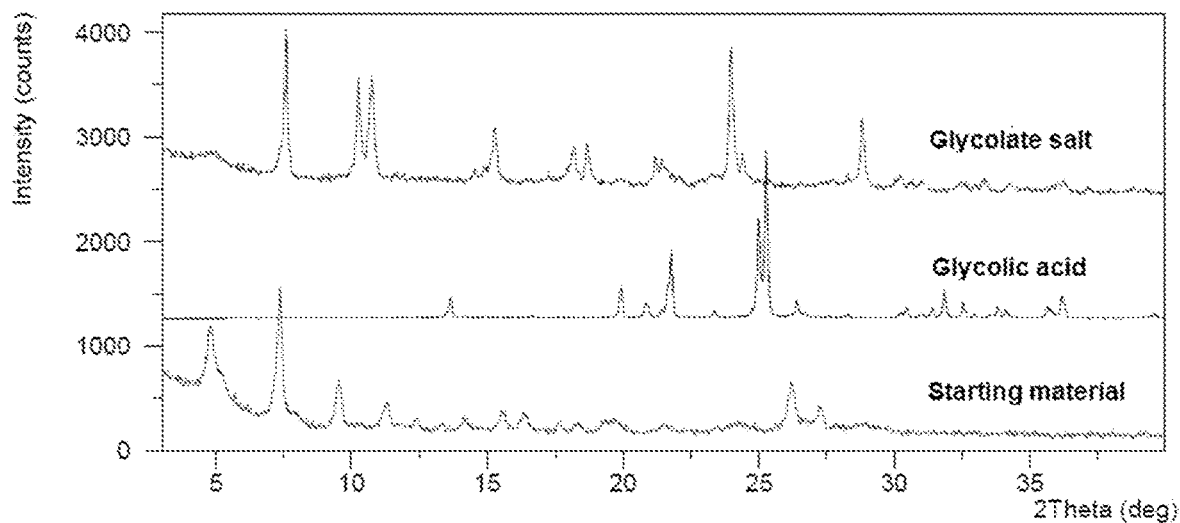
FIG. 16 shows an overlay of the X-ray diffraction diagrams of the crystalline glycolate salt of sepiapterin, of glycolic acid, and of the starting sepiapterin free base used in the preparation of the glycolate salt.

FIG. 16 shows the X-ray diffraction diagram of the crystalline glycolate salt of sepiapterin free base. The most intense peak in the X-ray diffraction diagram is observed at an angle of refraction 2θ of at least about 7.6°. In an essentially pure material of the crystalline glycolate salt of sepiapterin free base, peaks can be observed at angles of refraction 2θ as set forth in Table 20.

TABLE 20

| Position [2θ°] | Relative Intensity |
|---|---|
| 4.8 | 6.23 |
| 7.6 | 100.00 |
| 10.3 | 68.06 |
| 10.7 | 70.69 |
| 15.3 | 36.51 |

TABLE 20-continued

| Position [2θ°] | Relative Intensity |
|---|---|
| 18.2 | 24.25 |
| 18.7 | 27.26 |
| 19.9 | 2.66 |
| 21.2 | 17.11 |
| 24.0 | 96.62 |
| 24.4 | 18.44 |
| 28.8 | 47.57 |
| 30.3 | 7.43 |
| 32.5 | 4.42 |
| 33.3 | 7.49 |
| 34.3 | 5.21 |
| 36.3 | 7.37 |

The crystalline acetate salt of sepiapterin free base is characterized by peaks in the X-ray diffraction diagram observed at an angle of refraction 2θ at least at about 6.2°, about 12.0°, and about 18.1°.

Figure 17:
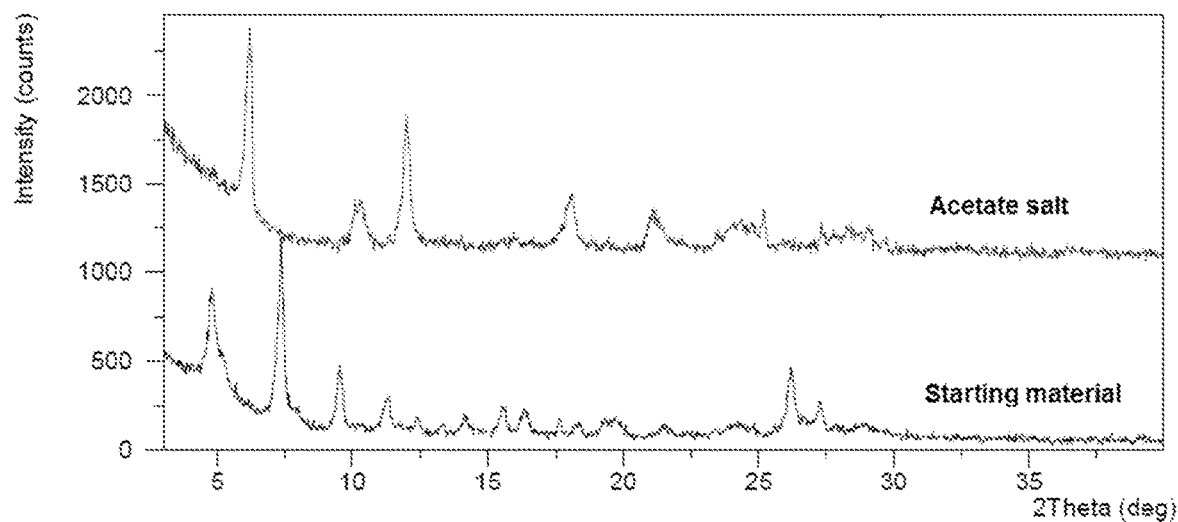
FIG. 17 shows an overlay of the X-ray diffraction diagrams of the crystalline acetate salt of sepiapterin and of the starting sepiapterin free base used in the preparation of the acetate salt.

FIG. 17 shows the X-ray diffraction diagram of the crystalline acetate salt of sepiapterin free base. The most intense peak in the X-ray diffraction diagram is observed at an angle of refraction 2θ of at least about 6.2°. In an essentially pure material of the crystalline acetate salt of sepiapterin free base, peaks can be observed at angles of refraction 2θ as set forth in Table 21.

TABLE 21

| Position [2θ°] | Relative Intensity |
|---|---|
| 6.2 | 100.00 |
| 10.2 | 23.29 |
| 12.0 | 71.59 |
| 18.1 | 31.27 |
| 21.1 | 20.29 |
| 24.2 | 14.92 |
| 25.2 | 23.03 |
| 27.3 | 13.30 |
| 29.1 | 12.95 |

The crystalline Form 1 sulfate salt of sepiapterin free base is characterized by peaks in the X-ray diffraction diagram observed at an angle of refraction 2θ at least at about 5.1°, about 7.8°, and about 23.0°.

Figure 18:
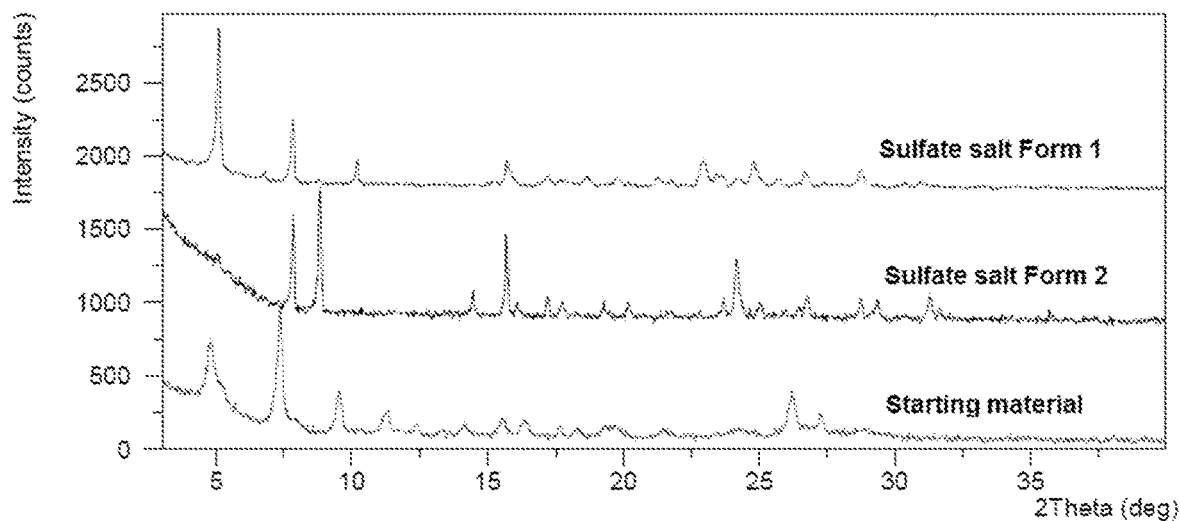
FIG. 18 shows an overlay of the X-ray diffraction diagrams of the crystalline sepiapterin Form 1 sulfate salt, of the crystalline sepiapterin Form 2 sulfate salt, and of the starting sepiapterin free base used in the preparation of the sulfate salts.

FIG. 18 shows the X-ray diffraction diagram of the crystalline Form 1 sulfate salt of sepiapterin free base. The most intense peak in the X-ray diffraction diagram is observed at an angle of refraction 2θ of at least about 5.1°. In an essentially pure material of the crystalline Form 1 sulfate salt of sepiapterin free base, peaks can be observed at angles of refraction 2θ as set forth in Table 22.

TABLE 22

| Position [2θ°] | Relative Intensity |
|---|---|
| 5.1 | 100.00 |
| 6.8 | 3.33 |
| 7.8 | 43.48 |
| 10.2 | 15.92 |
| 15.7 | 18.13 |
| 17.2 | 8.33 |
| 18.7 | 6.49 |
| 19.8 | 5.19 |
| 21.3 | 5.52 |
| 23.0 | 19.05 |
| 23.5 | 8.29 |
| 24.2 | 5.59 |
| 24.8 | 17.44 |
| 25.7 | 4.97 |
| 26.7 | 10.38 |

TABLE 22-continued

| Position [2θ°] | Relative Intensity |
|---|---|
| 28.7 | 11.49 |
| 30.4 | 2.88 |
| 31.0 | 3.67 |

The crystalline Form 2 sulfate salt of sepiapterin free base is characterized by peaks in the X-ray diffraction diagram observed at an angle of refraction 2θ at least at about 7.8°, about 8.8°, and about 24.1°.

FIG. 18 shows the X-ray diffraction diagram of the crystalline Form 2 sulfate salt of sepiapterin free base. The most intense peak in the X-ray diffraction diagram is observed at an angle of refraction 2θ of at least about 8.8°. In an essentially pure material of the crystalline Form 2 sulfate salt of sepiapterin free base, peaks can be observed at angles of refraction 2θ as set forth in Table 23.

TABLE 23

| Position [2θ°] | Relative Intensity |
|---|---|
| 5.0 | 4.71 |
| 7.9 | 72.24 |
| 8.8 | 100.00 |
| 14.5 | 19.26 |
| 15.7 | 59.40 |
| 16.1 | 8.69 |
| 17.2 | 14.82 |
| 17.7 | 10.89 |
| 19.3 | 9.92 |
| 20.2 | 9.60 |
| 23.7 | 15.38 |
| 24.2 | 43.88 |
| 25.0 | 11.44 |
| 26.8 | 16.81 |
| 28.7 | 16.07 |
| 29.4 | 13.84 |
| 31.3 | 17.14 |
| 31.7 | 7.26 |
| 35.7 | 5.75 |

In the context of stating that the crystalline hydrochloride salt of sepiapterin free base exhibits an X-ray diffraction diagram essentially as in FIG. 6, the term "essentially" means that at least the major peaks of the diagram depicted in FIG. 6, i.e. those having a relative peak intensity of more than 20%, especially more than 30%, as compared to the most intense peak in the diagram, have to be present. Alternatively, the crystalline hydrochloride salt of sepiapterin free base is characterized by a DSC curve showing an endotherm at 225.9° C.

In one preferred embodiment, the essentially pure crystalline hydrochloride salt of sepiapterin free base shows the X-ray diffraction diagram indicated in FIG. 6.

In another preferred embodiment, the crystalline hydrochloride salt of sepiapterin free base shows an X-ray diffraction diagram of the type shown in FIG. 6, in which the relative peak intensities of each peak do not deviate by more than 10% from the relative peak intensities in the diagram shown in FIG. 6, especially an X-ray diffraction diagram identical to that shown in FIG. 6.

In the context of stating that the crystalline salt forms of sepiapterin free base, such as the crystalline form 1 methanesulfonate salt, crystalline form 2 methanesulfonate salt, crystalline form 3 methanesulfonate salt, crystalline nicotinate salt, crystalline p-toluenesulfonate salt, crystalline benzenesulfonate salt, crystalline phosphate salt, crystalline malonate salt, crystalline L-tartrate salt, crystalline gentisate salt, crystalline fumarate salt, crystalline glycolate salt, crystalline acetate salt, crystalline form 1 sulfate salt, and crystalline form 2 sulfate salt, exhibits an X-ray diffraction diagram such as essentially as in FIGS. 7-18, respectively, the term "essentially" means that at least the major peaks of the diagram depicted in FIGS. 7-18, i.e., those having a relative peak intensity of more than 20%, especially more than 30%, as compared to the most intense peak in the diagram, have to be present.

In preferred embodiments, the essentially pure crystalline hydrochloride salt of sepiapterin free base shows the X-ray diffraction diagram indicated in FIG. 6.

In another preferred embodiment, the crystalline form 1 methanesulfonate salt, crystalline form 2 methanesulfonate salt, crystalline form 3 methanesulfonate salt, crystalline nicotinate salt, crystalline p-toluenesulfonate salt, crystalline benzenesulfonate salt, crystalline phosphate salt, crystalline malonate salt, crystalline L-tartrate salt, crystalline gentisate salt, crystalline fumarate salt, crystalline glycolate salt, crystalline acetate salt, crystalline form 1 sulfate salt, and crystalline form 2 sulfate salt of sepiapterin free base shows X-ray diffraction diagrams of the type shown in FIGS. 7-18, in which the relative peak intensities of each peak do not deviate by more than 10% from the relative peak intensities in the diagram shown in FIGS. 7-18, especially an X-ray diffraction diagram identical to that shown in FIGS. 7-18, respectively.

Alternatively, the crystalline form 1 methanesulfonate salt of sepiapterin free base is characterized by a DSC curve showing two endotherms at 186.0° C. and 229.1° C.;

the crystalline form 2 methanesulfonate salt of sepiapterin free base is characterized by a DSC curve showing three endotherms at 75.5° C., 182.6° C., and 234.9° C.;

the crystalline form 3 methanesulfonate salt of sepiapterin free base is characterized by a DSC curve showing two endotherms at 195.1° C. and 240.1° C.;

the crystalline nicotinate salt of sepiapterin free base is characterized by a DSC curve showing an endotherm at 221.9° C.;

the crystalline p-toluenesulfonate salt of sepiapterin free base is characterized by a DSC curve showing three endotherms at 77.2° C., 202.4° C. and 260.2° C.;

the crystalline benzenesulfonate salt of sepiapterin free base is characterized by a DSC curve showing two endotherms at 202.3° C. and 265.5° C.;

the crystalline phosphate salt of sepiapterin free base is characterized by a DSC curve showing three endotherms at 125.9° C., 152.1° C., and 157.6° C.;

the crystalline malonate salt of sepiapterin free base is characterized by a DSC curve showing a melting event at 115.8° C.;

the crystalline L-tartrate salt of sepiapterin free base is characterized by a DSC curve showing two endotherms at 97.2° C. and 160.6° C.;

the crystalline gentisate salt of sepiapterin free base is characterized by a DSC curve showing three endotherms at 70.5° C., 128.2° C., and 184.7° C.;

the crystalline fumarate salt of sepiapterin free base is characterized by a DSC curve showing two endotherms at 114.3° C. and 229.7° C.;

the crystalline glycolate salt of sepiapterin free base is characterized by a DSC curve showing two endotherms at 133.9° C. and 147.7° C.;

the crystalline acetate salt of sepiapterin free base is characterized by a DSC curve showing two endotherms at 146.1° C. and 175.4° C.; and the crystalline form 1 sulfate salt of sepiapterin free base is characterized by a DSC curve showing three endotherms at 94.5° C., 158.3° C., and 209.9° C.

In any of the above embodiments, the crystalline sepiapterin free base or a crystalline polymorph form of a salt of sepiapterin can occur as an anhydrate (e.g., without having any bound water or solvent or hydration or solvation) or as a hydrate, a partial hydrate (e.g., hemihydrate, sesquihydrate, and the like), as a dihydrate, a trihydrate, or the like, wherein the crystalline form binds a water of hydration or a solvent molecule associated with the crystalline form of sepiapterin or salt thereof. In an embodiment, crystalline sepiapterin Form B occurs as an anhydrate. In an embodiment, crystalline sepiapterin Form C occurs as a monohydrate or as a sesquihydrate. In an embodiment, crystalline sepiapterin Form D occurs as a monohydrate or as a sesquihydrate. In an embodiment, crystalline sepiapterin Form F occurs as a monohydrate or as a hemihydrate. In an embodiment, crystalline sepiapterin Form G occurs as an anhydrate.

In an embodiment, the invention provides a method for preparing crystalline Form D of sepiapterin. The method comprises preparing a slurry of sepiapterin in a liquid, wherein the liquid is water, acetone/water, isopropanol/isopropyl acetate, or tetrahydrofuran/n-hexane, and isolating sepiapterin Form D from the slurry. Preferably, the liquid is water. The sepiapterin Form D can be isolated using any suitable isolation method, for example, by centrifugation or by filtration. Preferably, the sepiapterin Form D is isolated by filtration. Typically, the sepiapterin Form D is further freed from solvent (e.g., water) by drying at room temperature.

In an embodiment, the invention provides a method for preparing crystalline Form F of sepiapterin. The method comprises preparing a slurry of sepiapterin in a solvent, wherein the solvent is water, acetone/water, isopropanol/isopropyl acetate, or tetrahydrofuran/n-hexane, and isolating sepiapterin Form D from the slurry. Preferably, the solvent is water. The sepiapterin Form D can be isolated using any suitable isolation method, for example, by centrifugation or by filtration. Preferably, the sepiapterin Form D is isolated by filtration. Sepiapterin Form D is then converted to Form F typically, by heating to 40-60° C. for 0.5-10 hours. Heating may be either at atmospheric pressure or under vacuum. Preferably heating is under vacuum.

Sepiapterin may serve as a useful therapeutic for diseases associated with low intracellular BH4 levels or with dysfunction of various BH4 dependent metabolic pathways including, but not limited to, primary tetrahydrobiopterin deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, and hypoglycemia. Thus, the various forms of sepiapterin in accordance with the present invention can be administered to a patient in an effective amount to obtain a treatment or amelioration of the disease, disorder or condition.

The present invention further provides a pharmaceutical composition comprising a crystalline sepiapterin free base or a crystalline polymorph form of a salt of sepiapterin as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intra-arterial, intramuscular, intraperitoneal, intrathecal, rectal, and vaginal administration are merely exemplary and are in no way limiting.

The crystalline sepiapterin free base or a crystalline polymorph form of a salt of sepiapterin can be used in the preparation of liquid formulations, such as in the form of a solution, suspension, or emulsion. Formulations suitable for oral administration can consist of (a) capsules, sachets, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for oral and/or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazopeak quaternary ammonium salts, and (3) mixtures thereof.

The parenteral formulations will typically contain from about 0.5 to about 25% by weight of the crystalline sepiapterin free base or a crystalline polymorph form of a salt of sepiapterin in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The crystalline sepiapterin free base or a crystalline polymorph form of a salt of sepiapterin of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one crystalline sepiapterin free base or a crystalline polymorph form of a salt of sepiapterin and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Additionally, the crystalline sepiapterin free base or a crystalline polymorph form of a salt of sepiapterin of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The crystalline sepiapterin free base or a crystalline polymorph form of a salt of sepiapterin can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically, the dosages range from about 0.001 to about 1000 mg/kg body weight of the patient being treated/day. For example, in embodiments, the crystalline sepiapterin free base or a crystalline polymorph form of a salt of sepiapterin may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In some embodiments, the crystalline sepiapterin free base or a crystalline polymorph form of a salt of sepiapterin can be formulated into unit solid oral dosage forms such as capsules or tablets. In these embodiments, each unit solid oral dosage form can comprise any suitable amount of the crystalline sepiapterin free base or a crystalline polymorph form of a salt of sepiapterin. For example, each solid oral dosage form can comprise about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 50 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 2000 mg, about 3000 mg, about 4000 mg, about 5000 mg, and the like.

The following examples further illustrate the invention but, of course, should not be construed as in any way limiting its scope.

Abbreviations: MeOH—methanol; DMSO—dimethylsulfoxide; EtOAc—ethyl acetate; DMAc—dimethylacetamide; THF—tetrahydrofuran; NMP—N-methylpyrrolidone.

For X-ray powder diffraction analysis, a PANalytical Empyrean X-ray powder diffractometer was used. The parameters are as follows:

| XRD Parameters | |
|---|---|
| Parameter | Value |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2θ) | 3°~40° |
| Scan step time (s) | 17.8 |
| Test time (s) | 5 min 30 s |

DSC was performed using a TA Q200/Q2000 DSC from TA Instruments. Parameters used are as follows:

| Parameters | DSC |
|---|---|
| Method | Ramp |
| Sample pan | Aluminum, crimped |
| Temperature | 25° C.-desired temperature |
| Heating rate | 10° C./min |
| Purge gas | $N_2$ |

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. As such, the following examples are provided to teach various aspects of the present invention. These examples represent individual embodiments of the aspects of this invention and one skilled in the art will recognize that additional examples can be generated in order to equally teach the aspects of the present invention.

Example 1

This example demonstrates a preparation of the crystalline Form B of sepiapterin free base in accordance with an embodiment of the invention.

73.2 mg of starting material sepiapterin was weighed into a 20-mL glass vial. 2.5 mL of N-methyl pyrrolidone (NMP) was added to dissolve the starting material. The solution was filtered into a new vial. 17 mL of acetonitrile (ACN) was added step-wise, with the sample stirring at RT with a rate of ~1000 rpm. The suspension was stirred at RT for 2 hrs. The resulting precipitate was isolated by centrifugation and dried in vacuum at RT for 3 hrs to obtain crystalline Form B of sepiapterin free base.

Example 2

This example demonstrates a preparation of crystalline Form C of sepiapterin free base in accordance with an embodiment of the invention.

100.4 mg of starting material sepiapterin was weighed into a 20-mL glass vial. 2 mL of ACN was added to form a suspension, which was stirred at 50° C. with a rate of ~1000 rpm. The resulting solids were isolated by centrifugation for 2 minutes through a 0.25 □m pore size centrifugation filter and drying at RT for approximately 12 hours to obtain crystalline Form C of sepiapterin free base.

Example 3

This example demonstrates a preparation of the crystalline Form D of sepiapterin free base in accordance with an embodiment of the invention.

200.1 mg of starting material sepiapterin was weighed into a 20-mL glass vial. 5 mL of $H_2O$ was added to form a suspension, which was stirred at 50° C. with a rate of ~1000 rpm. The resulting solids were isolated by centrifugation for 2 minutes through a 0.25 □m pore size centrifugation filter. One-half of the collected solids were dried at RT for approximately 12 hours at atmospheric pressure to obtain crystalline Form D of sepiapterin free base.

Example 4

This example demonstrates a preparation of the crystalline Form F of sepiapterin free base in accordance with an embodiment of the invention. The other half of the collected solids from Example 3 were dried under vacuum at 50° C. for 0.5 hr to obtain crystalline Form F of sepiapterin free base.

Example 5

This example demonstrates a preparation of the crystalline Form G of sepiapterin free base in accordance with an embodiment of the invention. The crystalline Form G of sepiapterin free base was prepared by heating a sample of crystalline Form F prepared as in Example 4 to 120° C. under $N_2$ flow.

Example 6

This example demonstrates a preparation of the crystalline hydrochloride salt of sepiapterin free base in accordance with an embodiment of the invention.

120.4 mg of sepiapterin freebase was weighed into a 20-mL glass vial. 0.8 mL of acetone/H$_2$O (9:1, v/v) and 42 µL of conc. HCl (37.5%) were added, and the resulting suspension was stirred at RT at a rate of ~1000 rpm for 5 days. The resulting solids were isolated by vacuum filtration and dried in vacuum at RT for 3 hrs.

The solids obtained above were dispersed in 3 mL of acetone/H$_2$O (9:1, v/v). 5.5 µL of conc. HCl (37.5%) was added and the suspension was stirred at RT at a rate of ~1000 rpm for 6 days, following which, the solids were isolated by vacuum filtration and dried in vacuum at RT overnight to obtain the crystalline hydrochloride salt of sepiapterin free base.

Example 7

This example demonstrates a preparation of the crystalline Form 3 methanesulfonate salt of sepiapterin free base in accordance with an embodiment of the invention.

51.7 mg of methanesulfonic acid was weighed into a 20-mL glass vial. 5 mL of MeOH was added to the vial. 120.7 mg of sepiapterin freebase was weighed into the vial. The resulting suspension was stirred at RT at a rate of ~1000 rpm for 5 days, following which 20 µL of methanesulfonic acid was added to the vial. The resulting mixture was stirred at RT at a rate of ~1000 rpm for 1 day. The solids were isolated by vacuum filtration and dried in vacuum at RT overnight. The dried solids were dispersed in 3 mL of MeOH and stirred at RT at a rate of ~1000 rpm for 1 day. The solids were isolated by vacuum filtration and dried in vacuum at RT overnight to obtain crystalline Form 3 methanesulfonate salt of sepiapterin free base.

Example 8

This example demonstrates a preparation of the crystalline nicotinate salt of sepiapterin free base in accordance with an embodiment of the invention.

119.5 mg of freebase was weighed into a 20-mL glass vial. 10 mL of MeOH was added to the vial. 100.1 mg of nicotinic acid was weighed into the vial. The resulting suspension was stirred at RT at a rate of ~1000 rpm for 7 hrs, following which the obtained solids were isolated by vacuum filtration and dried in vacuum at RT for 3 hrs to obtain the crystalline nicotinate salt of sepiapterin free base.

Example 9

This example demonstrates a preparation of the crystalline salt forms of sepiapterin free base in accordance with an embodiment of the invention.

Crystalline form 1 sulfate salt was obtained by slurrying equimolar amounts of starting material and H$_2$SO$_4$ in acetone/H$_2$O (9:1, v/v).

Crystalline form 2 sulfate salt was obtained by slurrying equimolar amounts of starting material and H$_2$SO$_4$ in THF/DMAc (9:1, v/v).

Crystalline p-toluenesulfonate salt was obtained by slurrying equimolar amounts of starting material and p-toluene sulfonic acid in methanol.

Crystalline Form 1 methanesulfonate salt was obtained by slurrying equimolar amounts of starting material and methane sulfonic acid in methanol.

Crystalline Form 2 methanesulfonate salt was obtained by slurrying equimolar amounts of starting material and methane sulfonic acid in acetone/H$_2$O (9:1, v/v).

Crystalline benzenesulfonate salt was obtained by slurrying equimolar amounts of starting material and benzene sulfonic acid in methanol.

Crystalline phosphate salt was obtained by slurrying equimolar amounts of starting material and H$_3$PO$_4$ in acetone/H$_2$O (9:1, v/v).

Crystalline malonate salt was obtained by slurrying starting material and malonic acid (molar ratio of acid/freebase about 5:1) in acetone/H$_2$O (9:1, v/v).

Crystalline L-tartrate salt was obtained by slurrying starting material and gentisic acid (molar ratio of acid/freebase about 4:1) in acetone/H$_2$O (9:1, v/v).

Crystalline gentisate salt was obtained by slurrying starting material and L-tartaric acid (molar ratio of acid/freebase about 5:1) in acetone/H$_2$O (9:1, v/v).

Crystalline fumarate salt was obtained by slurrying starting material and fumaric acid (molar ratio of acid/freebase about 5:1) in acetone/H$_2$O (9:1, v/v).

Crystalline glycolate salt was obtained by slurrying starting material and glycolic acid (molar ratio of acid/freebase about 4:1) in acetone/H$_2$O (9:1, v/v).

Crystalline acetate salt was obtained by slurrying starting material and acetic acid (molar ratio of acid/freebase about 5:1) in acetone/H$_2$O (9:1, v/v).

Example 10

This example demonstrates characterization of the starting sepiapterin used in the preparation of the crystalline polymorphs A, B, C, D, E, F, and G of sepiapterin free base and of the crystalline polymorph forms of salts of sepiapterin described herein.

A sample of sepiapterin free base was obtained commercially. DSC showed two endotherms at 82.8° C. and 179.8° C. The sepiapterin sample contained particles with an average particle size over 100 µm. The XRD pattern was determined before and after grinding to reduce the particle size such that it passes through a 140 mesh screen. The XRD patterns both before and after grinding are shown in FIG. 19. This polymorph of sepiapterin free base is referred to as Form A herein.

Example 11

This example demonstrates the results of stability studies carried out on the sepiapterin starting material (Form A), crystalline polymorph Form D, and crystalline polymorph Form F at temperatures of room temperature (RT), 35° C., and 50° C.

The purity of initial samples was determined by HPLC and was found to be as follows: Form A=99.3 area %, Form F=99.7 area %, Form D=99.1 area %, wherein area % refers to the area under the curve of the sepiapterin peak as compared with the total area under all of the peaks.

Form A and F samples were placed in chambers with silica gel to remove water (the relative humidity was measured to be ~10% RH) at different temperatures. Form D samples were placed in chambers with water (relative humidity was estimated to be ~100% RH) at different temperatures.

The HPLC purities and XRD patterns were obtained for each of Form A/F/D samples stored at various temperatures. The results after 1 week and 4 weeks of storage are set forth in Tables 22 and 23, respectively.

TABLE 24

| | | Storage after 1 week | | | | | | | |
|---|---|---|---|---|---|---|---|---|---|
| | | RT | | | 35° C. | | | 50° C. | | |
| Sample | Humidity | Purity (area %) | % of Initial | Form change | Purity (area %) | % of Initial | Form change | Purity (area %) | % of Initial | Form change |
| Form A | 10% RH | 98.8 | 99.5 | No | 98.0 | 98.6 | No | 95.2 | 95.8 | No |
| Form F | 10% RH | 99.4 | 99.7 | No | 99.4 | 99.7 | No | 99.2 | 99.4 | No |
| Form D | 100% RH | 99.0 | 99.9 | No | 98.8 | 99.7 | No | 98.5 | 99.3 | No |

TABLE 25

| | | Storage after 4 weeks | | | | | | | |
|---|---|---|---|---|---|---|---|---|---|
| | | RT | | | 35° C. | | | 50° C. | | |
| Sample | Humidity | Purity (area%) | % of Initial | Form change | Purity (area%) | % of Initial | Form change | Purity (area%) | % of Initial | Form change |
| Form A | 10% RH | 98.2 | 98.8 | No | 96.1 | 96.7 | No | 88.5 | 89.1 | No |
| Form F | 10% RH | 99.5 | 99.8 | No | 99.4 | 99.7 | No | 98.9 | 99.1 | No |
| Form D | 100% RH | 98.9 | 99.8 | No | 98.7 | 99.6 | No | 97.7 | 98.5 | No |

As is apparent from the results set forth in Tables 24 and 25, none of the samples exhibited a significant change in crystal structure as observed by XPD. Form A exhibited significantly less stability as determined by HPLC. After storage for 4 weeks at 50° C., the purity of Form A as measured by HPLC peak area % was 89.1% compared to the initial purity. The purities of Forms F and D were 99.1% and 98.5%, respectively, compared to the initial purity.

Example 12

This example demonstrates the stability of polymorphs D and F of sepiapterin free base on storage.

Samples of sepiapterin free base polymorph Forms D, F, and A were stored at room temperature (RT), 35° C., and 50° C. The samples were analyzed by HPLC at 1 week and 4 week intervals. The HPLC parameters were as follows:

| Parameters | Solubility | Stability (purity) |
|---|---|---|
| Column | Inertsil ODS-3, 4.6 × 250 mm, 5 μm | |
| Mobile phase | A: 20 mM $K_2HPO_4$-$KH_2PO_4$ buffer (pH 7.0) : ACN (98:2) | |

-continued

| Parameters | Solubility | | Stability (purity) | |
|---|---|---|---|---|
| | B: 20 mM $K_2HPO_4$-$KH_2PO_4$ buffer (pH 7.0) : ACN (50:50) | | | |
| Gradient table | Time (min) | % B | Time (min) | % B |
| | 0.0 | 0 | 0.0 | 0 |
| | 3.0 | 0 | 5.0 | 0 |
| | 10.0 | 100 | 25.0 | 100 |
| | 10.1 | 0 | 25.1 | 0 |
| | 12.0 | 0 | 35.0 | 0 |
| Run time | 12.0 min | | 35.0 min | |
| Post time | 0.0 min | | | |
| Flow rate | 1.0 mL/min | | | |
| Injection volume | 5 μL | | | |
| Detector wavelength | UV at 280 nm | | | |
| Column temperature | 40° C. | | | |
| Sampler temperature | RT | | | |
| Diluent | $H_2O$ | | | |

The results for polymorphs A, F, and D of sepiapterin free base are set forth in Tables 26-28.

TABLE 26

| | | Polymorph A | | | | | | |
|---|---|---|---|---|---|---|---|---|
| | | | RT/10% RH | | 35° C./10% RH | | 50° C./10% RH | |
| # | RRT | Initial | 1w | 4w | 1w | 4w | 1w | 4w |
| Impurity | 0.62 | 0.08 | 0.16 | 0.37 | 0.24 | 1.03 | 0.68 | 2.59 |
| Impurity | 0.89 | <0.05 | <0.05 | <0.05 | <0.05 | <0.05 | <0.05 | 0.06 |
| Impurity | 0.95 | 0.42 | 0.77 | 1.29 | 1.36 | 2.70 | 3.48 | 7.67 |
| Sepiapterin | 1.00 | 99.33 | 98.80 | 98.18 | 97.97 | 96.06 | 95.15 | 88.49 |
| Impurity | 1.06 | <0.05 | <0.05 | <0.05 | <0.05 | <0.05 | 0.45 | <0.05 |
| Impurity | 1.08 | <0.05 | 0.11 | <0.05 | 0.28 | <0.05 | 0.08 | 0.85 |
| Impurity | 1.17 | 0.17 | 0.16 | 0.16 | 0.16 | 0.16 | 0.16 | 0.17 |
| Impurity | 1.21 | <0.05 | <0.05 | <0.05 | <0.05 | <0.05 | <0.05 | 0.06 |
| Impurity | 1.25 | <0.05 | <0.05 | <0.05 | <0.05 | <0.05 | <0.05 | 0.11 |

TABLE 27

Polymorph F

| # | RRT | Initial | RT/10% RH 1w | RT/10% RH 4w | 35° C./10% RH 1w | 35° C./10% RH 4w | 50° C./10% RH 1w | 50° C./10% RH 4w |
|---|---|---|---|---|---|---|---|---|
| Impurity | 0.60 | <0.05 | <0.05 | <0.05 | <0.05 | <0.05 | <0.05 | 0.12 |
| Impurity | 0.95 | 0.09 | 0.29 | 0.30 | 0.35 | 0.42 | 0.58 | 0.86 |
| Sepiapterin | 1.00 | 99.74 | 99.42 | 99.54 | 99.43 | 99.43 | 99.15 | 98.85 |
| Impurity | 1.08 | <0.05 | 0.14 | <0.05 | 0.06 | <0.05 | 0.11 | <0.05 |
| Impurity | 1.17 | 0.17 | 0.16 | 0.16 | 0.15 | 0.15 | 0.15 | 0.17 |

TABLE 28

Polymorph D

| # | RRT* | Initial | RT/100% RH 1w | RT/100% RH 4w | 35° C./100% RH 1w | 35° C./100% RH 4w | 50° C./100% RH 1w | 50° C./100% RH 4w |
|---|---|---|---|---|---|---|---|---|
| Impurity | 0.62 | <0.05 | <0.05 | 0.09 | <0.05 | 0.09 | 0.08 | 0.14 |
| Impurity | 0.95 | 0.69 | 0.83 | 0.81 | 0.86 | 1.04 | 1.05 | 2.03 |
| Sepiapterin | 1.00 | 99.14 | 99.01 | 98.92 | 98.83 | 98.70 | 98.45 | 97.65 |
| Impurity | 1.08 | <0.05 | <0.05 | <0.05 | 0.14 | <0.05 | 0.26 | <0.05 |
| Impurity | 1.17 | 0.17 | 0.16 | 0.17 | 0.17 | 0.17 | 0.16 | 0.18 |

*Relative retention time

As is apparent from the results set forth in Tables 26-28, polymorphs D and F of sepiapterin free base exhibited significantly greater stability than polymorph A. The amount of sepiapterin in polymorph A decreased from 99.33% for 88.49% after storage for 4 weeks at 50° C./10% RH (relative humidity). The amount of sepiapterin in polymorph D decreased from 99.14% to 97.65% after storage for 4 weeks at 50° C./100% RH. The amount of sepiapterin in polymorph F decreased from 99.74% to 98.85% after storage for 4 weeks at 50° C./10% RH.

Example 13

This example demonstrates a preparation of crystalline Form E of sepiapterin free base.

100.6 mg of starting material was weighed into a 3-mL glass vial. 1 mL of MeOH was added to form a suspension. The sample was stirred at RT with a rate of ~1000 rpm. The resulting solids were isolated by centrifugation after 3 days and dried at RT overnight.

Other Embodiments

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. A pharmaceutical composition comprising crystalline Form D of sepiapterin free base having peaks at diffraction angle 2θ (°) of about 8.9°, about 10.3°, and about 26.0° as measured by X-ray diffractometry by irradiation with Cu Kα X-rays or calculated from X-ray diffractometry and a pharmaceutically acceptable carrier.

2. The pharmaceutical composition of claim 1, wherein the crystalline Form D is present in an amount of at least 90 percent by weight of the composition.

3. The pharmaceutical composition of claim 1, wherein the crystalline Form D is formulated as particles less than 100 μm in size.

4. The pharmaceutical composition of claim 1, wherein the crystalline Form D has peaks at diffraction angle 2θ (°) of about 8.9°, about 10.3°, about 10.9°, about 17.8°, about 24.9°, about 26.0°, about 26.7°, about 26.8°, and about 28.3° as measured by X-ray diffractometry by irradiation with Cu Kα X-rays or calculated from X-ray diffractometry.

5. A method of treating a tetrahydrobiopterin (BH4)-related disorder in a subject in need thereof, the method comprising administering an effective amount of the pharmaceutical composition of claim 1 to the subject, wherein the BH4-related disorder is selected from primary BH4 deficiency and phenylketonuria.

6. The method of claim 5, wherein the pharmaceutical composition is a liquid suspension.

7. A method of treating a tetrahydrobiopterin (BH4)-related disorder in a subject in need thereof, the method comprising administering an effective amount of crystalline Form D of sepiapterin free base having peaks at diffraction angle 2θ (°) of about 8.9°, about 10.3°, and about 26.0° as measured by X-ray diffractometry by irradiation with Cu Kα X-rays or calculated from X-ray diffractometry to the subject, wherein the BH4-related disorder is selected from primary BH4 deficiency and phenylketonuria.

8. The method of claim 7, wherein the crystalline Form D of sepiapterin free base is administered as a liquid suspension.

9. The method of claim 7, wherein the crystalline Form D has peaks at diffraction angle 2θ (°) of about 8.9°, about 10.3°, about 10.9°, about 17.8°, about 24.9°, about 26.0°, about 26.7°, about 26.8°, and about 28.3° as measured by X-ray diffractometry by irradiation with Cu Kα X-rays or calculated from X-ray diffractometry.

10. A method for decreasing phenylalanine levels in a subject in need thereof, the method comprising administering to the patient an effective amount of the pharmaceutical composition of claim 1 to the subject.

11. The method of claim 10, wherein the pharmaceutical composition is a liquid suspension.

12. A method for decreasing phenylalanine levels in a subject in need thereof, the method comprising administering an effective amount of crystalline Form D of sepiapterin free base having peaks at diffraction angle 2θ (°) of about 8.9°, about 10.3°, and about 26.0° as measured by X-ray diffractometry by irradiation with Cu Kα X-rays or calculated from X-ray diffractometry to the subject.

13. The method of claim 12, wherein the crystalline Form D of sepiapterin free base is administered as a liquid suspension.

14. The method of claim 12, wherein the crystalline Form D has peaks at diffraction angle 2θ (°) of about 8.9°, about 10.3°, about 10.9°, about 17.8°, about 24.9°, about 26.0°, about 26.7°, about 26.8°, and about 28.3° as measured by X-ray diffractometry by irradiation with Cu Kα X-rays or calculated from X-ray diffractometry.

15. A method of preparing a liquid formulation comprising dispersing crystalline Form D of sepiapterin free base having peaks at diffraction angle 2θ (°) of about 8.9°, about 10.3°, and about 26.0° as measured by X-ray diffractometry by irradiation with Cu Kα X-rays or calculated from X-ray diffractometry in a liquid.

16. The method of claim 15, wherein the liquid formulation is a suspension.

17. The method of claim 15, wherein the crystalline Form D has peaks at diffraction angle 2θ (°) of about 8.9°, about 10.3°, about 10.9°, about 17.8°, about 24.9°, about 26.0°, about 26.7°, about 26.8°, and about 28.3° as measured by X-ray diffractometry by irradiation with Cu Kα X-rays or calculated from X-ray diffractometry.

* * * * *